US008771713B2

(12) United States Patent
Peppas et al.

(10) Patent No.: US 8,771,713 B2
(45) Date of Patent: *Jul. 8, 2014

(54) METHOD AND PROCESS FOR THE PRODUCTION OF MULTI-COATED RECOGNITIVE AND RELEASING SYSTEMS

(75) Inventors: Nicholas A. Peppas, Austin, TX (US); Barbara Ekerdt, Austin, TX (US); Marta Gomez-Burgaz, Madrid (ES)

(73) Assignee: Board of Regents, The University of Texas System, Austin, TX (US)

( * ) Notice: Subject to any disclaimer, the term of this patent is extended or adjusted under 35 U.S.C. 154(b) by 334 days.

This patent is subject to a terminal disclaimer.

(21) Appl. No.: 12/396,540

(22) Filed: Mar. 3, 2009

(65) Prior Publication Data
US 2009/0232858 A1    Sep. 17, 2009

Related U.S. Application Data

(63) Continuation-in-part of application No. 12/047,309, filed on Mar. 12, 2008.

(60) Provisional application No. 60/894,451, filed on Mar. 12, 2007.

(51) Int. Cl.
*A61K 9/00* (2006.01)
*A61K 9/14* (2006.01)

(52) U.S. Cl.
USPC .............. 424/400; 424/486; 424/487; 526/72

(58) Field of Classification Search
USPC ............................. 424/400, 464, 486; 526/72
See application file for complete search history.

(56) References Cited

U.S. PATENT DOCUMENTS

| | | | |
|---|---|---|---|
| 3,538,214 A | 11/1970 | Polli et al. | |
| 4,228,149 A | 10/1980 | Brewer et al. | |
| 6,303,148 B1 | 10/2001 | Hennink et al. | |
| 6,897,271 B1 | 5/2005 | Domschke et al. | |
| 7,176,247 B1 | 2/2007 | Walker, Jr. | |
| 7,459,316 B2 | 12/2008 | Faid et al. | |
| 8,062,769 B2 | 11/2011 | Kai et al. | |
| 2002/0071877 A1 | 6/2002 | Mueller | |
| 2003/0059471 A1* | 3/2003 | Compton et al. | 424/489 |
| 2004/0091541 A1 | 5/2004 | Unger | |
| 2005/0008686 A1 | 1/2005 | Mannino et al. | |
| 2005/0249721 A1 | 11/2005 | Houston et al. | |
| 2005/0276781 A1 | 12/2005 | Ross et al. | |
| 2007/0027213 A1 | 2/2007 | Oberegger et al. | |
| 2007/0134721 A1 | 6/2007 | Laitenberger et al. | |
| 2008/0171067 A1 | 7/2008 | Govindan et al. | |
| 2008/0226684 A1 | 9/2008 | Peppas | |
| 2009/0081265 A1 | 3/2009 | Peppas | |
| 2009/0232857 A1 | 9/2009 | Peppas | |

FOREIGN PATENT DOCUMENTS

| | | |
|---|---|---|
| EP | 1664168 B1 | 3/2008 |
| WO | 02/071994 A1 | 9/2002 |
| WO | 2005/020849 A2 | 3/2005 |
| WO | 2006116734 A2 | 11/2006 |
| WO | 2008056746 | 5/2008 |
| WO | 2008112826 | 9/2008 |

OTHER PUBLICATIONS

Hilt et al., (Advanced Drug Delivery Reviews 56, 2004, pp. 1599-1620.*
Wizeman et al., Biomaterials, 22, 2001, pp. 1485-1491.*
International Search Report and Written Opinion for PCT/US2008/056746 dated Jun. 24, 2008.
Badiger, M. V., "Porogens in the preparation of microporous hydrogels based on poly(ethylene oxides)," Biomaterials (1993), 14:1059-1063.
Berman, H.M., et al., "The Protein Data Bank." Nucleic Acids Res., (2000), 28:235-242.
Bolisay, L.D.V., et al., "Separation of baculoviruses using configurationally biomimetic imprinted polymer hydrogels." Mat Res. Soc. Symp. Proc., (2004), 787: G3.1/1-G3.1/5.
Burt, S., "Essential Oils: their antibacterial properties and potential applications in food—a review." International Journal of Food Microbiology (2004), 94:223-253.
Byrne, M.E., et al., "Molecular imprinting within hydrogels." Adv. Drug Deliver. Rev., (2002), 54(1):149-161.
Byrne, M.E., et al., "Biomimetic Networks for Selective Recognition of Biomolecules." Materials Research Society. (2002) Abstract.
Cederfur, J., et al., "Synthesis and Screening of a Configurationally biomimetic imprinted Polymer Library Targeted for Penicillin G." J. Comb. Chem., (2003), 5:67-72.
Chang, C.P., et al., "Preparation of alginate complex capsules containing eucalyptus essential oil and its controlled release." Colloids and Surfaces B: Biointerfaces (2003) 32:257-262.
Duclairoir, C., et al., "Evaluation of gliadins nanoparticles as drug delivery systems: a study of three different drugs." International Journal of Pharmaceutics, (2003), 253:133-144.
Hilt, J.Z., et al., "Ultrasensitive Biomems Sensors Based on Microcantilevers Patterned with Environmentally Responsive Hydrogels." Biomedical Microdevices, (2003), 5(3):177-184.
Kabiri, K., et al., Novel approach to highly porous superabsorbent hydrogels: synergistic effect of porogens on porosity and swelling rate, Polymer International (2003), 52:1158-1164.
Liang, C., et al., "Molecular imprinting polymer coated BAW biomimic sensor for direct determination of epinephrine." Anal. Chim. Acta, (2000), 415:135-141.
Mosbach, K., "Toward the next generation of molecular imprinting with emphasis on the formation, by direct molding, of compounds with biological activity(biomimetics)." Anal. Chim. Acta, (2001), 435:3-8.
Omidian, H., et al., "Advances in superporous hydrogels," J Controlled Release (2005), 102:3-12.
Oral, E. et al., "Responsive and recognitive hydrogels using star polymers." J. Biomed. Mater. Res. A, (2004), 68:439-447.

(Continued)

*Primary Examiner* — Renee Claytor
*Assistant Examiner* — Shobha Kantamneni
(74) *Attorney, Agent, or Firm* — Chainey P. Singleton; Edwin S. Flores; Chalker Flores, LLP

(57) ABSTRACT

The present invention includes compositions, methods, systems for the controlled delivery of an active agent in a tablet polymer comprising two or more layers, wherein each of the two or more layers comprises at least one active agent and at least one molecular recognition polymer, wherein the two or more layers are compressed into a single tablet.

20 Claims, 4 Drawing Sheets

(56) References Cited

OTHER PUBLICATIONS

Parmpi, P. et al., "Biometric glucose recognition using configurationally biomimetic imprinted hydrogels." Biomaterials, (2004), 25:1969-1973.
Peppas, N.A., et al., "Controlled Release of fragrance from polymers I. Thermodynamic analysis." Journal of Controlled Release (1996), 40:245-250.
Peppas, N.A., et al., "Controlled release of perfumes from polymers. II. Incorporation and release of essential oils from glassy polymers," Journal of Applied Polymer Science, (1997), 66:509-513.
Peppas, N.A. et al., "Advances in Biomaterials, Drug Delivery, and Bionanotechnology." AIChE J., (2003), 49:2990-3006.
Rachkov, A., et al., "Towards Configurationally biomimetic imprinted Polymers Selective to Peptides and Proteins." The Epitope Approach. Biochimica et Biophysica Acta, (2001), 1544:255-266.
Secouard, S., et al., "Release of limonene from polysaccharide matrices: viscosity and synergy effect." Food Chemistry (2003), 82:227-234.
Yu, C., et al., "Influence of mobile phase composition and crosslinking density on the enantiomeric recognition properties of configurationally biomimetic imprinted polymers." J. Chromatogr. A, (2000), 888:63-72.
Peppas, Nicholas A., et al., "New Biomaterials for Intelligent Biosensing, Recognitive Drug Delivery and Therapeutics," Department of Pharmaceutics, Chemical and Biomedical Engineering, 1 University Station, C-0400, The University of Texas at Austin, Austin, Texas 78712-0231, pp. 25-38, 2003.
Alvarez-Lorenzo, et al. "Polymer Gels That Memorize Elements of Molecular Conformation" Macromolucules 2000, 33, 8693-8697.
Alvarez-Lorenzo, et al. "Simultaneous Multiple-Point Adsorption of Aluminum Ions and Charged Molecules by a Polyampholyte Thermosensitive Gel: Controlling Frustrations in a Heteropolymer Gel" Langmuir 2001, 17, 3616-3622.
Alvarez-Lorenzo, et al. "Soft Contact Lenses Capable of Sustained Delivery of Timolol" Journal of Pharmaceutical Sciences, vol. 91, No. 10, Oct. 2002.
Alvarez-Lorenzo, et al. "Reversible adsorption of calcium ions by imprinted temperature sensitive gels" Journal of Chemical Physics, vol. 114, No. 6, Feb. 8, 2001.
Andersson, et al. "Mimics of the binding sites of opioid receptors obtained by molecular imprinting of enkephalin and morphine" Proc. Natl. Acad. Sci. USA, vol. 92, pp. 4788-4792, May 1995, Biochemistry.
Andersson, et al. "Imprinting of Amino Acid Derivatives in Macroporous Polymers" Tetrahedron Letters, vol. 25, No. 45, pp. 5211-5214,1984.
Ansel!, et al. "Molecularly imprinted polymers for bioanalysis: chromatography, binding assays and biomimetic sensors" Current Opinion in Biotechnology 1996:7:89-94.
Appella, et al. B-Peptide Foldamers: Robust Helix Formation in a New Family of B-Amino Acid Oligomers J. Am. Chem. Soc. 1996, 118, 13071-13072.
Bartsch, Richard A. and Mizuo Maeda "Molecular and Ionic Recognition with Imprinted Polymers: A Brief Overview"—Book Abstract—8 pp.
Bashir, et al. "Micromechanical cantilever as an ultrasensitive pH microsensor" Applied Physics Letters, vol. 81, No. 16, Oct. 14, 2002.
Bergmann, et al. "Protein-Imprinted Polymeric Microparticles for Tissue Engineering Applications" 2003 Society for Biomaterials 29th Annual Meeting Transactions, Trans Soc. Biomat 2003:29:457.
Breinl, et al. "Chemical Investigation of the Precipitate from Hemoglobin and Anti-hemoglobin Serum and Remarks on the Nature of Antibodies" Z. Physiol. Chem., 1930. 192: p. 45.
Bures, et al. "Surface modifications and molecular imprinting of polymers in medical and pharmaceutical applications" Journal of Controlled Release 72 (2001) 25-33.
Burnet, F.M. "A Modification of Jerne's Theory of Antibody Production using the Concept of Clonal Selection" Reprinted from The Australian Journal of Science 20 (3): 67-69, 1957. CA—A Cancer Journal for Clinicians, vol. 26, No. 2 Mar./Apr. 1976 119.
Burton, Dennis R. "Monoclonal Antibodies from Combinatorial Libraries" Acc. Chem. Res. 1993,26, 405-411.
Byrne, et al. "Biomimetic Networks for Selective Recognition of Biomolecules" Mat. Res. Soc. Symp. Proc. vol. 724, 2002 Materials Research Society N9.3.
Byrne, et al. "Networks for Recognition of Biomolecules: Molecular Imprinting and Micropatterning Poly(ethylene glycol)—Containing Films" Polym. Adv. Technol 13, 798-816 (2002).
Byrne, M.E. Biomimetic Materials for Recognition of Biomolecules: Recognitive Networks for Drug Delivery and Bionanotechnology, in Chemical Engineering. Dec. 2003, Thesis, Purdue University: West Lafayette, IN.
Byrne, et al. "Micropatterning Biomimetic Materials for Bioadhesion and Drug Delivery" Purdue University: West Lafayette, IN. pp. 443-470.
Byrne, et al. "Molecular imprinting within hydrogels" Advanced Drug Delivery Reviews 54 (2002) 149-161.
Canal, et al. "Correlation between mesh size and equilibrium degree of swelling of polymeric networks" Journal of Biomedical Materials Research, vol. 23, 1183-1193 (1989).
Chen, et al. "Molecular Recognition: Design of Keys" Combinatorial Chemistry & High Throughput Screening, 2002, 5, 409-427.
Cormack, et al. "Molecular imprinting: recent developments and the road ahead" Reactive & Functional Polymers 41 (1999) 115-124.
Dado, et al. "Intramolecular Hydrogen Bonding in Derivatives of B-Alanine and y-Amino Butyric Acid: Model Studies for the Folding of Unnatural Polypeptide Backbones" J. Am. Chem. Soc. 1994,116, 1054-1062.
Davies, et al. "J. Am. Chem. Soc. 1994,116, 1054-1062" Acc. Chem. Res. 1993,26, 421-427.
Duclairoir et al., "Evaluation of gliadins nanoparticles as drug delivery systems: a study of three different drugs" International Journal of Pharmaceutics 253 (2003) 133-144.
Egholm, et al. "Peptide Nucleic Acids (PNA). Oligonucleotide Analogues with an Acbiral Peptide Backbone" J. Am. Chem. Soc1. 992,114, 1895-1897.
Franzois, et al. "Insecticidal and Genotoxic Activities of Mint Essential Oils" J. Agric. Food Chem. 1997, 45, 2690-2694.
Gellman, Samuel H. "Foldamers: A Manifesto" Acc. Chem. Res. 1998, 31, 173-180.
Harris, et al. "Refined Structure of an Intact IgG2a Monoclonal Antibody" Biochemistry 1997, 36, 1581-1597.
Hartmans, et al. "Report of the Meeting of the Section Physiology of the EAPR, Jun. 20-24, 1994" Potato Research, 37 (1994) pp. 435-463.
Hartmans, et al. "Use of talent (carvone) as a sprout growth regulator of seed potatoes and the effect on stm and tuber number" Potato Research, 41 (1998) pp. 190-191.
Haupts, et al. "Imprinted polymer-based enantioselective acoustic sensor using a quartz crystal microbalance" Anal. Commun., 1999, 36, 391-393.
Hilt, et al. "Novel Biomimetic Polymer Networks: Development and Application as Selective Recognition Elements for Biomolecules at the Micro-/Nano-scale" in AIChE Nanoscale Science and Engineering Topical Conference Proceedings. 2003. San Francisco, CA.
Hilt, et al. Ultrasensitive biomens sensors based on microcantilevers patterned with enviromentally responsive hydrogels. Biomed Microdevices 2003;5:177-184.
Hilt, et al. "Configurational biomimesis in drug delivery: molecular imprinting of biologically significant molecules" Advanced Drug Delivery Reviews 56 (2004) 1599-1620.
Hilt, J. Zachary "Nanotechnology and biomimetic methods in therapeutics: molecular scale control with some help from nature" Advanced Drug Delivery Reviews 56 (2004) 1533-1536.
Jerne, Niels K. "The Natural-Selection Theory of Antibody Formation" Proc. Natl. Acad. Sci. USA, 1955. 41: p. 849-857.
Karmalkar, et al. "Molecularly Imprinted Hydrogels Exhibit Chymotrypsin-like Activity" Macromolecules 1996,29, 1366-1368.
Kempe, et al. "Separation of amino acids, peptides and proteins on molecularly imprinted stationary phases" Journal of Chromatography A, 691 (1995) 317-323.

(56) References Cited

OTHER PUBLICATIONS

Kempe, et al. "An Approach Towards Surface Imprinting Using the Enzyme Ribonuclease A" Journal of Molecular Recognition, vol. 8, 35-39 (1995).
Kirshenbaum, et al. "Sequence-specific polypeptoids: A diverse family of heteropolymers with stable secondary structure" Proc. Natl. Acad. Sci. USA, vol. 95, pp. 4303-4308, Apr. 1998.
Kirshenbaum, et al. "Designing Polymers that Mimic Biomolecules" Current Opinion in Structural Biology 1999, 9:530-535.
Koehl, et al. "De Novo Protein Design. I. In Search of Stability and Specificity" J.Mol. Biol. (1999) 293, 1161-1181.
Koehl, et al. "De Novo Protein Design. II. Plasticity in Sequence Space" J. Mol. Biol. (1999) 293, 1183-1193.
Kohler, G. "Derivation and diversification of monoclonal antibodies" The EMBO Journal, vol. 4, No. 6, pp. 1359-1365, 1985.
Kohler, et al. "Continuous cultures of fused cells secreting antibody of predefined specificity" Nature, vol. 256, Aug. 7, 1975.
Kriz, et al. "Thin-Layer Chromatography Based on the Molecular Imprinting Technique" Anal. Chem. 1994, 66, 2636-2639.
Merrifield, R.B. "Solid Phase Peptide Synthesis. II. The Synthesis of Bradykinin" J. Am. Chem. Soc., 1964. 86: p. 304.
Merrifield, R.B. "Solid-Phase Peptide Synthesis, III. An Improved Synthesis of Bradykinin" Biochem, 1964. 3: p. 1385-1390.
Andersson, et al. "Study of the nature of recognition in molecularly imprinted polymers, II. [1] Influence of monomer-template ratio and sample load on retention and selectivity" J. Chromatogr. A, 1999. 848: p. 39-49.
Herr, et al., J. Am. Chem. Soc. 89:4808-09 (1967).
Jerne, N.K. "The Generative Grammar of the Immune System, in Nobel Lectures" Physiology or Medicine 1981-1990, J. Lindsten, Editor. 1993, World Scientific Publishing Co.: Singapore. p. 211-225.
Komiyama, et al. "Molecular Imprinting From Fundamentals to Applications" 2003, Weinheim, Germany: Wiley-VCH.
Merrifield, R.B. "Solid Phase Peptide Synthesis. I. The Synthesis of a Tetrapeptide" J. Am. Chem. Soc., 1963. 85: p. 2149-2154.
Merrifield, R.B.. "Solid Phase Synthesis, in Nobel Lectures" Chemistry 1981-1990, T. Frängsmyr, Editor. 1992, World Scientific Publishing Co.: Singapore. p. 149-175.
Milstein, C. "From the Structure of Antibodies to the Diversification of the Immune Response, in Nobel Lectures" Physiology or Medicine 1981-1990, J. Lindsten, Editor. 1993, World Scientific Publishing Co.: Singapore. p. 248-270.
Mosbach, et al. "Molecular Imprinting: Status Arils et Quo Vadere, in Molecular and Ionic Recogniton with Imprinted Polymers" R.A. Bartsch and M. Maeda, Editors. 1998, American Chemical Society: Washington, D.C.
Mosbach, et al. "The Emerging Technique of Molecular Imprinting and its Future Impact on Biotechnology" Biotechnol., 1996. 14: p. 163-170.
Pande, et al. "Thermodynamic procedure to synthesize heteropolymers that can renature to recognize a given target molecule" Proc. Natl. Acad. Sci. USA, 1994. 91: p. 12976-12979.
Pande, et al. "How to Create Polymers with Protein-Like Capabilities: A Theoretical Suggestion" Physica D, 1997. 107: p. 316-321.
Pande, et al. "Phase diagram of heteropolymers with an imprinted conformation" Macromolecules, 1995. 28: p. 2218-2227.
Pande, et al. "Folding Thermodynamics and kinetics of imprinted renaturable heteropolymers" J. Chem. Phys., 1994. 101(9): p. 8246-8257.
Pauling, L. "A Theory of the Structure and Process of Formation of Antibodies" J. Am. Chem. Soc., 1940. 62: p. 2643-2657.
Peppas, N. A., "Intelligent biomaterials as pharmaceutical carriers in microfabricated and nanoscale devices." MRS Bulletin (2006), 31:888-893.
Ramström, et al. "Synthesis and catalysis by molecularly imprinted materials" Curr. Opin. Chem. Biol., 1999. 3: p. 759-764.
Ratner, B.D. "The Engineering of Biomaterials Exhibiting Recognition and Specificity" J. Mol. Recognition, 1996. 9: p. 617-625.
Robinson, et al. "Molecular imprinting of a transition state analogue leads to a polymer exhibiting esterolytic activity" J. Chem. Soc. Chem. Commun., 1989. 14: p. 969-970.
Sanchez, et al. "Migration models for polymer additives" Polym. News 6 (1980) 249-256.
Sanchez, I.C. "Equilibrium distribution of a minor constituent between a polymer and its environment, in Durability of Macromolecular Materials" R.K. Eby, ed. ACS Symp. Ser. vol. 95, American Chemical Society, Washington, DC, 1979, pp. 171-181.
Sellergren, et al. "Enantioselective ester hydrolysis catalyzed by imprinted polymers" Tetrahedron-Asymmetry, 1994. 5: p. 1403-1406.
Shakhnovich, et al. "Engineering of stable and fast-folding sequences of model proteins" Proc. Natl. Acad. Sci. USA, 1993. 90: p. 7195-7199.
Shnek, et al. "Specific Protein Attachment to Artificial Membranes via Coordination to Lipid-Bound Copper(II)" Langmuir, 1994. 10: p. 2382-2388.
Talmage, D.W. "Allergy and Immunology" Ann. Rev. Med., 1957. 8: p. 239.
Tormo, et al. "Crystal Structure of a Human Rhinovirus Neutralizing Antibody Complexed with a Peptide Derived from Viral Capsid Protein VP2" EMBO J., 1994. 13: p. 2247-2256.
Vlatakis, et al. "Drug assay using antibody mimics made by molecular imprinting" Nature, 1993. 361: p. 645-647.
Venton, et al. "Influence of protein on polysiloxane polymer formation: evidence for induction of complementary protein-polymer interactions" Biochim. Biophys. Acta, 1995. 1250: p. 126-136.
Ward, J., et al., "Micropatterning of biomedical polymer surfaces by novel UV polymerization techniques." J Biomed Mater Res (2001), 56:351-360.
Wulff, et al. "Enzyme-Analogue Built Polymers and Their Use for the Resolution of Racemates" Tetrahedron Letters, 1973. 44: p. 4329-4332.
Wulff, G., et al., "Enzyme-Analogue Built Polymers. 4. Synthesis of Polymers Containing Chiral Cavities and Their Use for Resolution of Racemates." Makromolekulare Chemie-Macromolecular Chemistry and Physics (1977), 178:2799-2816.
Wulff, G., et al., "Enzyme-analogue built polymers. 5. Specificity distribution of chiral cavities prepared in synthetic-polymers." Makromolekulare Chemie-Macromolecular Chemistry and Physics (1977), 178:2817-2825.
Yue, et al. "Inverse Protein Folding Problem: Designing Polymer Sequences" Proc. Natl. Acad. Sci. USA, 1992. 89: p. 4163-4167.

* cited by examiner

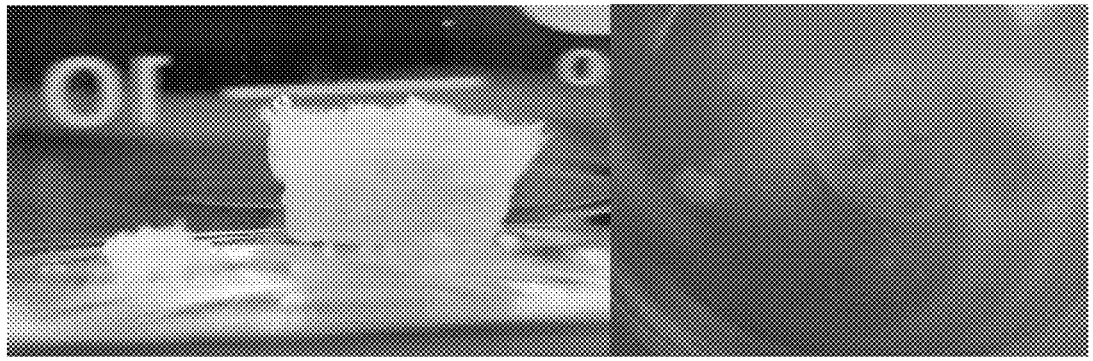
FIGURES 7A                    FIGURE 7B
FIGURES 8A                    FIGURE 8B
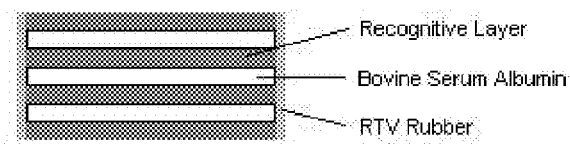
FIGURE 9

METHOD AND PROCESS FOR THE PRODUCTION OF MULTI-COATED RECOGNITIVE AND RELEASING SYSTEMS

CROSS-REFERENCE TO RELATED APPLICATIONS

This application claims priority to U.S. Provisional Application Ser. No. 60/894,451, filed Mar. 12, 2007, and is a continuation-in-part application of U.S. patent application Ser. No. 12/047,309, filed Mar. 12, 2008, the entire contents of which are incorporated herein by reference.

TECHNICAL FIELD OF THE INVENTION

The present invention relates in general to the field of the controlled release of agents, and more particularly, to novel compositions and methods for making controlled release configurational biomimetic imprinting networks.

STATEMENT OF FEDERALLY FUNDED RESEARCH

None.

BACKGROUND OF THE INVENTION

Without limiting the scope of the invention, its background is described in connection with the recognition and controlled release of active agents from polymers.

This invention relates generally to the field of microencapsulation, and, more particularly, to the development of microparticles and nanoparticles with multiple recognitive layers. In general, microencapsulation is achieved with fluidized bed processes. The fluidized bed coating process is a widely used technique for large particle size. Small particles coated in a fluidized bed tend to agglomerate and adhere to the wall of the bed due to the electrostatic charge and capillary forces resulting from the remaining solvent.

Despite improvements in the range of particle sizes, other limitations exist in optimizing microcapsules to be applied in a variety of applications; in particular, the loading and delivery of therapeutic agents. It is therefore a need to optimize the particle coating process for the formation and drug delivery vehicles. It is a further need to have optimization to the Wurster process to form multiple-layers for increased functionality, especially as drug delivery systems with multiple recognitive layers.

SUMMARY OF THE INVENTION

The needs of the invention set forth above as well as further and other needs and advantages of the present invention are achieved by the embodiments of the invention described herein below.

In one embodiment, the present invention comprises a tablet polymer comprising two or more layers, wherein each of the two or more layers comprises at least one active agent and at least one molecular recognition polymer, wherein the two or more layers are compressed into a single tablet. In one aspect, the polymer comprises microparticles and may also include at least one of an adhesive, a binder, an inactive matrix or an excipient. In one aspect, the polymer is at least one of biocompatible, biodegradable, swellable, water-soluble, or porous. In another aspect, the recognitive portion of the layer is disrupted due to: osmosis upon the presence and binding of the molecule leading to rupture due to swelling; change of the solubility of the polymeric network leading to polymer dissolution; local temperature changes leading to expansion of the polymeric network and combinations thereof. In another aspect, the active agent is loaded into two or more layers, e.g., 3, 4, 5, 6, 7, 8, 9, 10, 11, 12, 13, 14, 15, 16, 17, 18, 19 or 20 layers. In another aspect, the active agent is selected from pharmaceuticals, medical agents, food components, detergents, bleaches, fabric softeners, fragrances, cosmetic products, air fresheners, room deodorant devices, perfumed substrates, perfumed plastics and pet collars. In one aspect, the polymer is selected from Poly(allylamine), Acrylic acid, Acrylamide, (Diethylamino)ethyl methacrylate, (Ethylamino)methacrylate, Methacrylic acid, methylmethacrylate, Triazacyclononane-copper(II) complex, 2-(methacryloyxloxy) ethyl phosphate, methacrylamide, 2-(trifluoromethyl)acrylic acid, 3-aminophenylboronic acid, poly(allylamine), o-phthalic dialdehyde, oleyl phenyl hydrogen phosphate, 4-vinylpyridine, vinylimidazole, 2-acryloilamido-2,2'-methopropane sulfonic acid, Silica, organic silanes, N-(4-vinyl)-benzyl iminodiacetic acid, Ni(II)-nitrilotriacetic acid, N-acryloyl-alanine, ethylene glycol dimethacrylate, pentaerythritol triacrylate, pentaerythritol tetraacrylate, trimethylolpropane trimethacrylate, vinyl triethoxysilane, vinyl trimethoxysilane, toluene 2,4-diisocyanate, epichlorohydrin, triglycerolate diacrylate, polystyrene surface, Propylene glycol dimethacrylate, poly(ethylene glycol) n dimethacrylate, methacrylate derived silica, acrylonitrile, N,N'-dimethylacrylamide, poly(ethylene glycol)diacrylate. The tablet may further comprise a coating. In one aspect, the tablet is a sphere, film, planar, semi-spherical, cylinder, rod, hemispheres, conical, hemi-cylinders, bi-layer and combination thereof.

Another embodiment of the present invention is a composition that comprises a tablet polymer comprising two or more layers, wherein each of the two or more layers comprises at least one active agent and at least one molecular recognition polymer, wherein the two or more layers are compressed into a single tablet.

Yet another aspect of the present invention is a method of making a recognitive release system with limited swelling upon exposure to solvent alone comprising: selecting one or more molecules for imprinting and one or more active agent; forming two or more polymeric recognitive network layers about the one or more molecules and the active agent; removing the molecule from the first and a second polymeric recognitive network; and compressing the two or more layers into a tablet. In one aspect, the method further comprised the step of coating the tablet. In another aspect, the two or more layers are formed about a core. In yet another aspect, the two or more layers are coated into multiple layers. In one aspect, the tablet is formed into a sphere, film, planar, semi-spherical, cylinder, rod, hemispheres, conical, hemi-cylinders and combination thereof. In one aspect, the polymeric recognitive network is at least partially porous. In one aspect, the polymer comprises microparticles. In one aspect, the layers further comprise at least one of an adhesive, a binder, an inactive matrix or an excipient. In one aspect, the polymer is at least one of biocompatible, biodegradable, swellable, water-soluble, or porous. In one aspect, the composition comprises 3, 4, 5, 6, 7, 8, 9, 10, 11, 12, 13, 14, 15, 16, 17, 18, 19 or 20 layers.

Examples of active agents for use with the present invention include pharmaceutical and medical applications, food components, detergents, bleaches, fabric softeners, fragrances, cosmetic products, air fresheners, room deodorant devices, perfumed substrates, perfumed plastics and pet collars. Other actives include food and cosmetic applications that use hydrocolloids as imprinting carriers for polymers of high molecular weight, wherein the hydrocolloids are extracted from plants, seaweeds or animal collagen, produced by microbial synthesis, and comprise polysaccharides, proteins and combinations thereof. The molecule-imprinted network may be a carbohydrate polymer of glycosidic type mono-sugar repeative units, galactomannans, pectins, alginates, carrageenans and xanthan gum that are linear or branched, neutral or anionic and combinations thereof. Other examples include household products selected from laundry care; paper products; specialty cleaners (chlorinated cleaners, scouring pads, effervescent toilet bowl cleaner powders); air fresheners and combinations thereof. Further examples include personal care products selected from hair care (shampoos, hair mousses, styling agents); skin care (body lotions, vitamin e, aloe vera); bath products (moisture-triggered release products); body powders; toilet soap (milled or poured, ionic strength-triggered release) and combinations thereof. Also, cosmetics and treatment products selected from lipstick; eye-liner; foundation; base; blush; mascara; eye shadow; lip liner; facial powder; consealer; facial cream; make-up remover; mascara remover; make-up; skin treatments and may even include one or more fragrances or carriers therefore that include cologne; perfume; sampling; antiperspirant; deodorant; anti-dandruff shampoos; athlete foot products and combinations thereof. Other actives include a surfactant, a bleaching agent, a corrosion inhibitor, a sudsing modifier, a fluorescent whitening agent, one or more enzymes, an anti redeposition agent, a color, a fragrance, one or more additives and combinations thereof.

The present invention also include the release of active agent upon exposure to the cognate molecule or moiety that ultimately causes release upon a loss of structural integrity caused by, e.g., changes in solubility, pressure, a pH shift, a change in temperature, a temperature increase, enzymatic breakdown, diffusion and combinations thereof. The skilled artisan will also be able to be formed integrally or as a coating for controlled release or one or more layers of the active, the recognitive polymer or both. Furthermore, the polymeric recognitive network may be formed into one or more layers, each of which recognizes a different molecule, a different active or inert agent or both. The polymeric recognitive network is formed into a sphere, film, planar, semi-spherical, cylinder, rod, hemispheres, conical, hemi-cylinders and combination thereof and may also be at least partially porous. The polymeric recognitive network also may be formed into one or more layers, each of which recognizes a different molecule, and where a different active or inert agent may be contained between polymeric layers.

BRIEF DESCRIPTION OF THE DRAWINGS

For a more complete understanding of the features and advantages of the present invention, reference is now made to the detailed description of the invention along with the accompanying figures and in which:

FIG. 3a is a 7-layer tablet made from 5 wt % cellulose and 20 wt % PNVP; the thickness was approx. 1.5 mm. FIG. 3b is a single-layer tablet from the same mixture, with a thickness of approx. 0.36 mm.

FIG. 4a shows how a single-layer tablet in DI water cracked and crumbled to bottom after 20 min. Notice how a big part is still floating on top while part that cracked off is lying on bottom. FIG. 4b shows how a single-layer tablet in 100 mg/dL D-glucose solution cracked after 60 minutes.

FIG. 5a shows the single-layer tablet after 18 hours in DI water. FIG. 5b shows the single-layer tablet after 18 hours in 100 mg/dL D-glucose and DI water.

FIGS. 7a and 7b. These photos show a piece that fell off the top of a 9-layer tablet placed in 100 mg/dL glucose solution after 13 minutes FIGS. 8a and 8b. These photos show the 9-layer tablet placed in 100 mg/dL glucose solution after several hours (FIG. 8a) and 20 hours (FIG. 8b).

FIG. 9. A diagram indicating the several layers of an ideal multilaminate system.

DETAILED DESCRIPTION OF THE INVENTION

Figures 1A, 1B:
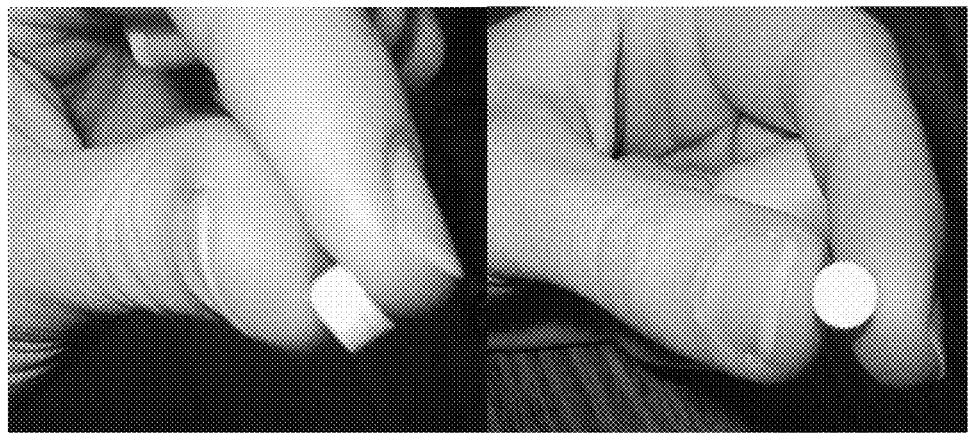
FIG. 1. Multilayer tablets with 9 layers from the first recipe. The thickness is approximately 3 mm and diameter is 6.33 mm.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "active agent(s)," "active ingredient(s)," "pharmaceutical ingredient(s)," and "bioactive agent(s)" are defined as drugs and/or pharmaceutically active ingredients. The present invention may be used to encapsulate, attach, bind or otherwise be used to affect the storage, stability, longevity and/or release of any of the following drugs as the pharmaceutically active agent in a composition. One or more of the following bioactive agents may be combined with one or more carriers and the present invention (which may itself be the carrier):

Analgesic anti-inflammatory agents such as, acetaminophen, aspirin, salicylic acid, methyl salicylate, choline salicylate, glycol salicylate, 1-menthol, camphor, mefenamic acid, fluphenamic acid, indomethacin, diclofenac, alclofenac, ibuprofen, ketoprofen, naproxene, pranoprofen, fenoprofen, sulindac, fenbufen, clidanac, flurbiprofen, indoprofen, protizidic acid, fentiazac, tolmetin, tiaprofenic acid, bendazac, bufexamac, piroxicam, phenylbutazone, oxyphenbutazone, clofezone, pentazocine, mepirizole, and the like.

Drugs having an action on the central nervous system, for example sedatives, hypnotics, antianxiety agents, analgesics and anesthetics, such as, chloral, buprenorphine, naloxone, haloperidol, fluphenazine, pentobarbital, phenobarbital, secobarbital, amobarbital, cyclobarbital, codeine, lidocaine, tetracaine, dyclonine, dibucaine, cocaine, procaine, mepivacaine, bupivacaine, etidocaine, prilocaine, benzocaine, fentanyl, nicotine, and the like. Local anesthetics such as, benzocaine, procaine, dibucaine, lidocaine, and the like.

Antihistaminics or antiallergic agents such as, diphenhydramine, dimenhydrinate, perphenazine, triprolidine, pyrilamine, chlorcyclizine, promethazine, carbinoxamine, tripelennamine, brompheniramine, hydroxyzine, cyclizine, meclizine, clorprenaline, terfenadine, chlorpheniramine, and the like. Anti-allergenics such as, antazoline, methapyrilene, chlorpheniramine, pyrilamine, pheniramine, and the like. Decongestants such as, phenylephrine, ephedrine, naphazoline, tetrahydrozoline, and the like.

Antipyretics such as, aspirin, salicylamide, non-steroidal anti-inflammatory agents, and the like. Antimigrane agents such as, dihydroergotamine, pizotyline, and the like. Acetonide anti-inflammatory agents, such as hydrocortisone, cortisone, dexamethasone, fluocinolone, triamcinolone, medrysone, prednisolone, flurandrenolide, prednisone, halcinonide, methylprednisolone, fludrocortisone, corticosterone, paramethasone, betamethasone, ibuprophen, naproxen, fenoprofen, fenbufen, flurbiprofen, indoprofen, ketoprofen, suprofen, indomethacin, piroxicam, aspirin, salicylic acid, diflunisal, methyl salicylate, phenylbutazone, sulindac, mefenamic acid, meclofenamate sodium, tolmetin, and the like. Muscle relaxants such as, tolperisone, baclofen, dantrolene sodium, cyclobenzaprine.

Steroids such as, androgenic steriods, such as, testosterone, methyltestosterone, fluoxymesterone, estrogens such as, conjugated estrogens, esterified estrogens, estropipate, 17-β estradiol, 17-β estradiol valerate, equilin, mestranol, estrone, estriol, 17β ethinyl estradiol, diethylstilbestrol, progestational agents, such as, progesterone, 19-norprogesterone, norethindrone, norethindrone acetate, melengestrol, chlormadinone, ethisterone, medroxyprogesterone acetate, hydroxyprogesterone caproate, ethynodiol diacetate, norethynodrel, 17-α hydroxyprogesterone, dydrogesterone, dimethisterone, ethinylestrenol, norgestrel, demegestone, promegestone, megestrol acetate, and the like.

Respiratory agents such as, theophilline and β2-adrenergic agonists, such as, albuterol, terbutaline, metaproterenol, ritodrine, carbuterol, fenoterol, quinterenol, rimiterol, solmefamol, soterenol, tetroquinol, and the like. Sympathomimetics such as, dopamine, norepinephrine, phenylpropanolamine, phenylephrine, pseudoephedrine, amphetamine, propylhexedrine, arecoline, and the like.

Antimicrobial agents including antibacterial agents, antifungal agents, antimycotic agents and antiviral agents; tetracyclines such as, oxytetracycline, penicillins, such as, ampicillin, cephalosporins such as, cefalotin, aminoglycosides, such as, kanamycin, macrolides such as, erythromycin, chloramphenicol, iodides, nitrofrantoin, nystatin, amphotericin, fradiomycin, sulfonamides, purrolnitrin, clotrimazole, miconazole chloramphenicol, sulfacetamide, sulfamethazine, sulfadiazine, sulfamerazine, sulfamethizole and sulfisoxazole; antivirals, including idoxuridine; clarithromycin; and other anti-infectives including nitrofurazone, and the like.

Antihypertensive agents such as, clonidine, α-methyldopa, reserpine, syrosingopine, rescinnamine, cinnarizine, hydrazine, prazosin, and the like. Antihypertensive diuretics such as, chlorothiazide, hydrochlorothrazide, bendoflumethazide, trichlormethiazide, furosemide, tripamide, methylclothiazide, penfluzide, hydrothiazide, spironolactone, metolazone, and the like. Cardiotonics such as, digitalis, ubidecarenone, dopamine, and the like. Coronary vasodilators such as, organic nitrates such as, nitroglycerine, isosorbitol dinitrate, erythritol tetranitrate, and pentaerythritol tetranitrate, dipyridamole, dilazep, trapidil, trimetazidine, and the like. Vasoconstrictors such as, dihydroergotamine, dihydroergotoxine, and the like. β-blockers or antiarrhythmic agents such as, timolol pindolol, propranolol, and the like. Humoral agents such as, the prostaglandins, natural and synthetic, for example PGE1, PGE2α, and PGF2α, and the PGE1 analog misoprostol. Antispasmodics such as, atropine, methantheline, papaverine, cinnamedrine, methscopolamine, and the like.

Calcium antagonists and other circulatory organ agents, such as, aptopril, diltiazem, nifedipine, nicardipine, verapamil, bencyclane, ifenprodil tartarate, molsidomine, clonidine, prazosin, and the like. Anti-convulsants such as, nitrazepam, meprobamate, phenyloin, and the like. Agents for dizziness such as, isoprenaline, betahistine, scopolamine, and the like. Tranquilizers such as, reserprine, chlorpromazine, and antianxiety benzodiazepines such as, alprazolam, chlordiazepoxide, clorazeptate, halazepam, oxazepam, prazepam, clonazepam, flurazepam, triazolam, lorazepam, diazepam, and the like.

Antipsychotics such as, phenothiazines including thiopropazate, chlorpromazine, triflupromazine, mesoridazine, piperracetazine, thioridazine, acetophenazine, fluphenazine, perphenazine, trifluoperazine, and other major tranqulizers such as, chlorprathixene, thiothixene, haloperidol, bromperidol, loxapine, and molindone, as well as, those agents used at lower doses in the treatment of nausea, vomiting, and the like.

Drugs for Parkinson's disease, spasticity, and acute muscle spasms such as levodopa, carbidopa, amantadine, apomorphine, bromocriptine, selegiline (deprenyl), trihexyphenidyl hydrochloride, benztropine mesylate, procyclidine hydrochloride, baclofen, diazepam, dantrolene, and the like. Respiratory agents such as, codeine, ephedrine, isoproterenol, dextromethorphan, orciprenaline, ipratropium bromide, cromglycic acid, and the like. Non-steroidal hormones or antihormones such as, corticotropin, oxytocin, vasopressin, salivary hormone, thyroid hormone, adrenal hormone, kallikrein, insulin, oxendolone, and the like.

Vitamins such as, vitamins A, B, C, D, E and K and derivatives thereof, calciferols, mecobalamin, and the like for dermatologically use. Enzymes such as, lysozyme, urokinaze, and the like. Herb medicines or crude extracts such as, Aloe vera, and the like.

Antitumor agents such as, 5-fluorouracil and derivatives thereof, krestin, picibanil, ancitabine, cytarabine, and the like. Anti-estrogen or anti-hormone agents such as, tamoxifen or human chorionic gonadotropin, and the like. Miotics such as pilocarpine, and the like.

Cholinergic agonists such as, choline, acetylcholine, methacholine, carbachol, bethanechol, pilocarpine, muscarine, arecoline, and the like. Antimuscarinic or muscarinic cholinergic blocking agents such as, atropine, scopolamine, homatropine, methscopolamine, homatropine methylbromide, methantheline, cyclopentolate, tropicamide, propantheline, anisotropine, dicyclomine, eucatropine, and the like.

Mydriatics such as, atropine, cyclopentolate, homatropine, scopolamine, tropicamide, eucatropine, hydroxyamphetamine, and the like. Psychic energizers such as 3-(2-aminopropy)indole, 3-(2-aminobutyl)indole, and the like.

Antidepressant drugs such as, isocarboxazid, phenelzine, tranylcypromine, imipramine, amitriptyline, trimipramine, doxepin, desipramine, nortriptyline, protriptyline, amoxapine, maprotiline, trazodone, and the like.

Anti-diabetics such as, insulin, and anticancer drugs such as, tamoxifen, methotrexate, and the like.

Anorectic drugs such as, dextroamphetamine, methamphetamine, phenylpropanolamine, fenfluramine, diethylpropion, mazindol, phentermine, and the like.

Anti-malarials such as, the 4-aminoquinolines, alphaminoquinolines, chloroquine, pyrimethamine, and the like.

Anti-ulcerative agents such as, misoprostol, omeprazole, enprostil, and the like. Antiulcer agents such as, allantoin, aldioxa, alcloxa, N-methylscopolamine methylsuflate, and the like. Antidiabetics such as insulin, and the like.

Anti-cancer agent such as, cis-platin, actinomycin D, doxorubicin, vincristine, vinblastine, etoposide, amsacrine, mitoxantrone, tenipaside, taxol, colchicine, cyclosporin A, phenothiazines or thioxantheres.

For use with vaccines, one or more antigens, such as, natural, heat-killer, inactivated, synthetic, peptides and even T cell epitopes (e.g., GADE, DAGE, MAGE, etc.) and the like.

Example therapeutic or active agents also include water soluble or poorly soluble drug of molecular weigh from 40 to 1,100 including the following: Hydrocodone, Lexapro, Vicodin, Effexor, Paxil, Wellbutrin, Bextra, Neurontin, Lipitor, Percocet, Oxycodone, Valium, Naproxen, Tramadol, Ambien, Oxycontin, Celebrex, Prednisone, Celexa, Ultracet, Protonix, Soma, Atenolol, Lisinopril, Lortab, Darvocet, Cipro, Levaquin, Ativan, Nexium, Cyclobenzaprine, Ultram, Alprazolam, Trazodone, Norvasc, Biaxin, Codeine, Clonazepam, Toprol, Zithromax, Diovan, Skelaxin, Klonopin, Lorazepam, Depakote, Diazepam, Albuterol, Topamax, Seroquel, Amoxicillin, Ritalin, Methadone, Augmentin, Zetia, Cephalexin, Prevacid, Flexeril, Synthroid, Promethazine, Phentermine, Metformin, Doxycycline, Aspirin, Remeron, Metoprolol, Amitriptyline, Advair, Ibuprofen, Hydrochlorothiazide, Crestor, Acetaminophen, Concerta, Clonidine, Norco, Elavil, Abilify, Risperdal, Mobic, Ranitidine, Lasix, Fluoxetine, Coumadin, Diclofenac, Hydroxyzine, Phenergan, Lamictal, Verapamil, Guaifenesin, Aciphex, Furosemide, Entex, Metronidazole, Carisoprodol, Propoxyphene, Digoxin, Zanaflex, Clindamycin, Trileptal, Buspar, Keflex, Bactrim, Dilantin, Flomax, Benicar, Baclofen, Endocet, Avelox, Lotrel, Inderal, Provigil, Zantac, Fentanyl, Premarin, Penicillin, Claritin, Reglan, Enalapril, Tricor, Methotrexate, Pravachol, Amiodarone, Zelnorm, Erythromycin, Tegretol, Omeprazole, and Meclizine.

The drugs mentioned above may be used in combination as required. Moreover, the above drugs may be used either in the free form or, if capable of forming salts, in the form of a salt with a suitable acid or base. If the drugs have a carboxyl group, their esters may be employed. The acid mentioned above may be an organic acid, for example, methanesulfonic acid, lactic acid, tartaric acid, fumaric acid, maleic acid, acetic acid, or an inorganic acid, for example, hydrochloric acid, hydrobromic acid, phosphoric acid or sulfuric acid. The base may be an organic base, for example, ammonia, triethylamine, or an inorganic base, for example, sodium hydroxide or potassium hydroxide. The esters mentioned above may be alkyl esters, aryl esters, aralkyl esters, and the like. Also with sugar to release as a bitterness masking agent (sugar as the agent).

The bioactive may also be administered, e.g., parenterally, intraperitoneally, intraspinally, intravenously, intramuscularly, intravaginally, subcutaneously, or intracerebrally. Dispersions may be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier may be a solvent or dispersion medium containing, for example, water, ethanol, poly-ol (for example, glycerol, propylene glycol, and liquid polyethylene glycol, and the like), suitable mixtures thereof, and vegetable oils.

The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent that delays absorption, for example, aluminum monostearate or gelatin.

Sterile injectable solutions may be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier that contains a basic dispersion medium and the required other ingredients from those enumerated above. In the case of sterile powders for the preparation of sterile injectable solutions, the methods of preparation may include vacuum drying, spray drying, spray freezing and freeze-drying that yields a powder of the active ingredient (i.e., the therapeutic compound) plus any additional desired ingredient from a previously sterile-filtered solution thereof.

The bioactive may be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied as will be known to the skilled artisan. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a subject.

Aqueous compositions of the present invention comprise an effective amount of the nanoparticle, nanofibril or nanoshell or chemical composition of the present invention dissolved and/or dispersed in a pharmaceutically acceptable carrier and/or aqueous medium. The biological material should be extensively dialyzed to remove undesired small molecular weight molecules and/or lyophilized for more ready formulation into a desired vehicle, where appropriate. The active compounds may generally be formulated for parenteral administration, e.g., formulated for injection via the intravenous, intramuscular, subcutaneous, intralesional, and/or even intraperitoneal routes. The preparation of an aqueous composition that contain an effective amount of the nanoshell composition as an active component and/or ingredient will be known to those of skill in the art in light of the present disclosure. Typically, such compositions may be prepared as injectables, either as liquid solutions and/or suspensions; solid forms suitable for using to prepare solutions and/or suspensions upon the addition of a liquid prior to injection may also be prepared; and/or the preparations may also be emulsified.

The present inventor has developed methods and techniques to form synthetic biomimetic networks, gels or polymers that will bind and respond to specific molecules, analytes or moieties. These biomimetic polymer networks, gels or polymers are advantageous because they can be tailored to bind any molecule with controlled selectivity and affinity.

There are some significant characteristics to consider in the design of a biomimetic polymer networks via a configurational biomimetic imprinting (CBIP) technique. To achieve a relatively easy on/off binding event, a non-covalent recognition process is favored. Therefore, supramolecular interactions, such as hydrogen bonding, electrostatic interactions, hydrophobic interactions, and van der Waals forces, are employed to achieve recognition. For the formation of the network, it is imperative that the functional monomers, crosslinker, and template are mutually soluble. In addition, the solvent must be chosen wisely, so that it does not interact and destabilize the self-assembled functional monomer and template.

The ability to engineer traditional polymers with specific material properties is hampered by lack of control of molecular weight, chain configuration and polymerization kinetics. Hybrid materials have been developed to preserve the bulk properties of traditional polymers while making their molecular chains look more like proteins. The elusive goal of molecular recognition in synthetic polymer systems has been reached in certain cases. Polyacrylic gels have been designed as with recognition capabilities by incorporating non-covalently crosslinked antibodies. These proteins couple the reversible swelling character of the networks with molecular recognition by only swelling in the presence of a specific antigen. The advantage of using synthetic polymeric materials based solely on proteins or peptides is the high degree of control over properties. Peptides and proteins can be coded for specific properties using a basic knowledge of inter and intrachain interactions. The present and future of biomedical materials development requires a degree of control prediction in design, synthesis and function of next generation materials. Recent work with this principle in mind has resulted in protein-based materials with properties analogous to more widely used polymers as well as new properties. These new materials have been generated with a variable degree of efficiency and complexity.

Examples of monomers that may be used to form polymers for use with the present invention include: Poly(allylamine), Acrylic acid, Acrylamide, (Diethylamino)ethyl methacrylate, (Ethylamino)methacrylate, Methacrylic acid, methylmethacrylate, Triazacyclononane-copper(II) complex, 2-(methacryloyxloxy)ethyl phosphate, methacrylamide, 2-(trifluoromethyl)acrylic acid, 3-aminophenylboronic acid, poly(allylamine), o-phthalic dialdehyde, oleyl phenyl hydrogen phosphate, 4-vinylpyridine, vinylimidazole, 2-acryloilamido-2,2'-methopropane sulfonic acid, Silica, organic silanes, N-(4-vinyl)-benzyl iminodiacetic acid, Ni(II)-nitrilotriacetic acid, N-acryloyl-alanine. These monomers may be combined with one or more crosslinkers to achieve the desired low or minimal swelling upon exposure to solvent alone that include: ethylene glycol dimethacrylate, pentaerythritol triacrylate, pentaerythritol tetraacrylate, trimethylolpropane trimethacrylate, vinyl triethoxysilane, vinyl trimethoxysilane, toluene 2,4-diisocyanate, epichlorohydrin, triglycerolate diacrylate, polystyrene surface, Propylene glycol dimethacrylate, poly(ethylene glycol) n dimethacrylate, methacrylate derived silica, acrylonitrile, N,N'-dimethylacrylamide, poly(ethylene glycol)diacrylate. Examples of solvents that may be used to achieve low or minimal swelling include Acetonitrile, Acetic acid, ethanol, aqueous buffer, toluene, water, chloroform, hexane, methanol, tetrahydrofuran.

The development of drug delivery vehicles requires systems that respond to a specific cue in the biological environment before the release of a drug payload. This is also coupled with the desire for such new devices to otherwise maintain structural integrity and avoid clearance from the body. We have described sensitive gels with stimuli-sensitive recognition very similar to recognition in proteins. By outlining the principles developed by analyzing theoretical mechanics of heteropolymers, the underlying memory of macromolecule conformation is discovered and empirically verified. Essentially, their design includes polymerizing in the presence of target molecule, functional monomer, thermo-sensitive monomer, and end shielded post-crosslinking monomer. Some of these adsorption sites were destroyed upon gel swelling and reformed upon shrinking. Important contributions have been made describing the nature of recognition in low cross-linked systems, and it is only a matter of time when intelligent gels can recognize other types of molecules.

The present invention includes imprinted gels or chains possessing certain macromolecular architecture with binding abilities could be used as the sensing elements within analyte sensitive controlled release systems. Analyte sensitive polymer networks have been the focus of much research (mostly saccharide recognition) and have been designed in a number of ways.

Balancing pharmaceutical research for new drugs to treat human illness and disease with economic factors to minimize the cost of drug therapy has led to controlled and targeted drug delivery products. The goal of controlled drug delivery is to reduce the cost of treatment by allowing smaller, yet equally effective, dosages through a regulating device. Some drugs have very short half-lives in the human body, and large doses of these drugs are metabolized rapidly, while other drugs, such as many of the new protein drugs, are very fragile in the harsh environment inside the body. Controlled release devices can prolong the release time for the former, allowing effective dosages, and can protect sensitive drugs until the point where they are to be delivered.

In the past, drug delivery devices have been limited to systems such as tablets, capsules, powders, droplets, ointments and injections. Such systems while useful in treating some diseases have certain disadvantages: (1) they are difficult to regulate drug delivery; (2) they deliver their bioactive agent (drug) relatively fast; and (3) agent delivery is usually decreasing with time It must be noted that although the description above uses a drug as an active agent, similar problems have been observed with release of delivery of other active or bioactive agents, such as (but not limited to): pesticides, herbicides, other agricultural products, molluscicides, other marine biology products, agents that kill ticks, flees, etc., essential oils, perfumes, agents used in kitchen products, whitening agents used in laundry detergents.

More recently, systems have been developed which allow controlled release of drugs to targeted areas of the body. Some methods used for the controlled delivery of drugs include: inserts and implants, transdermal systems, oral delivery systems, nasal delivery systems, vaginal delivery systems, rectal delivery systems, ocular delivery systems and bioadhesive/mucoadhesive systems.

Most of these systems while solving the problem of prolonged delivery of active agents, are not as efficacious in applications when the patient is unwilling or unable to take the necessary drug (payload) at a specific time or specific interval. More precisely, such systems cannot control the problem of patient compliance, a significant problem in this industry.

The use of carriers sensitive to the surrounding environment, such as pH-sensitive or temperature-sensitive systems have been reported in the field. Indeed, investigators have reported methods of delivering drugs, active agents and bioactive agents in response to changes in pH or temperature of the surrounding fluid.

Clearly, such systems can improve the pattern of delivery by being triggered to release their payload when a particular pH prevails in the surrounding fluid. For example, numerous drug delivery systems have been patented where the passage from the stomach (low pH) to the upper small intestine (high pH) triggers the release of an active compound (drug). Often, such systems are accompanied by selective targeting to various tissue sites. For example, the so-called mucoadhesive drug delivery systems are based on polymeric materials which adhere to the mucin layer of a biological membrane for some length of time. The desired drug is loaded into the polymers. Once introduced to the body, the polymer carrier begins to swell, allowing the release of the drug. Because the polymer binds to the mucin layer of the membrane, the drug is released locally and is thought to be able to absorb more easily across the membrane into the bloodstream. Some possible routes of administration for mucoadhesive systems include: the nasal, ocular, buccal, gastrointestinal, vaginal and rectal areas.

There are several distinct advantages in using controlled release systems over other methods of drug delivery. First, the drug can be delivered at a relatively constant concentration. Thus, the drug concentration can be maintained at a level that is higher than the therapeutic level of the drug, but lower than the toxic level. In the case of tablets, the drug concentration steadily increases until all of the drug has been released. At this point the concentration of drug in the body may be above its toxic level. Once the drug has been released from the tablet the concentration decreases until a subsequent dose is taken. A second advantage of this type of drug delivery is that the rate and time period of delivery can be controlled depending on the properties of the polymer system.

However, the previous systems do not possess the additional advantage of intelligence of recognition of not just a change in pH or temperature, but in response to a finite concentration of an external analyte, a compound with special desirable or undesirable properties.

Most if not all of these systems, whether passive of pH- or T-sensitive have a structure that belongs to the category of hydrogels. Hydrogels are highly biocompatible which makes them appropriate for a number of pharmaceutical and medical (but also cosmetic, food and consumer) applications. In addition to drug delivery carriers, hydrogels are biomaterials used as contact lenses and scaffolds for tissue engineering applications to name only a few of the potential roles. The polymer network can contain homopolymers or copolymers with the chemical structure determining the properties of the hydrogel.

The network structure of the hydrogel can be characterized by a number of parameters. Three parameters that I will discuss here are the polymer volume fraction in the swollen state, $v_{2,s}$, the molecular weight between crosslinks, $M_c$, and the distance between crosslinks also known as the mesh size. The values for these parameters can be determined empirically or by theoretical calculations.

The polymer fraction in the swollen state is a measure of how much water the hydrogel can imbibe when placed in an aqueous environment. The ability of hydrogels to retain large amounts of water makes them similar to natural tissue and may contribute to their high biocompatibility. Both the molecular weight and distance between crosslinks give an indication of how highly crosslinked the network is. Due to the randomness involved with polymer formation, these parameters can only be given as average values throughout the hydrogel. These parameters can indicate how much space is available for diffusion in and out of the hydrogel. This value, along with the size of the agent to be delivered, will be important in determining the release kinetics of the agent from the hydrogel in drug delivery applications. The degree of swelling present in the network will affect the mesh size and therefore a physiologically-responsive hydrogel that swells when presented with certain stimuli can have different release kinetics at different sites in the body.

pH-Responsive hydrogels are composed of ionic networks and swell in response to pH changes. This swelling behavior is controlled by the ionization of the pendant groups in the network. Charged groups exhibit electrostatic repulsion that leads to imbibition of water and increased mesh size. This event also depends on the level of crosslinking present in the hydrogel. Highly crosslinked materials will not be able to swell to as high a degree as materials with lower crosslinking ratios due to decreased chain mobility. The degree to which a hydrogel network will swell is also dependent upon the ability to imbibe water. Hydrogels with hydrophilic groups can imbibe more water than those with hydrophobic groups and can therefore swell to a greater extent. The hydrophobicity/hydrophilicity of the network will therefore also have an impact on the diffusion of any compound embedded within a hydrogel network. An example of a monomer that will create an ionic hydrogel with pH-responsive swelling is methacrylic acid (MAA). When the pH of the environment is greater than the $pK_a$ of the carboxylic acid groups in MAA, they become ionized and cause interchain repulsion. The $pK_a$ of this group in poly(methacrylic acid) is approximately 4.9 making the pH shift from the stomach to upper small intestine (1.5-6) appropriate to change the ionization of the carboxyl groups. The charged groups are also hydrophilic and allow water to enter the network and continue the swelling process.

The process of ionization is reversible depending on the pH of the environment. If the MAA is grafted with another polymer capable of forming hydrogen bonds, like poly(ethylene glycol) (PEG), then hydrogen bonds can form between the chains when in the protonated state at low pH. This pH-dependant formation of hydrogen bonds provides another means by which the network exists in a compact state at low pH and a more open state at the elevated pH. Hydrogels that exhibit this activity are termed pH-responsive complexation hydrogels.

Through the use of monomers with side chains containing groups with $pK_a$ values in the range desired, a pH-responsive hydrogel could be designed much in the same manner as enteric coatings. Hydrogels can exhibit swelling to different degrees based on the intensity of the stimulus and this could be used to target release of multiple compounds at different sites. For example, if a hydrogel swelled and increased it mesh size sufficiently to release a small compound at one pH and showed increased swelling at a pH later in the gastrointestinal tract, like the colon as opposed to the small intestine, it could release a second larger agent at this location. The variability of the hydrogel delivery system in what it will respond to and how it will respond makes it an attractive candidate for numerous clinical applications including targeted drug delivery.

These hydrogels can be used for delivery of a variety of therapeutic agents. For example, previous work in our laboratory has focused on the use of hydrophilic polymer carriers for oral delivery of proteins such as insulin. The loading of proteins into the hydrogels was done by imbibition, where the polymer is swollen in a solution containing the protein and collapsed at low pH to trap the protein inside.

Recognitive Materials—Molecular Recognition. The recognition of a specific molecule out of a whole host of competing species is essential to all life processes. It is this ability that allows for the proper functioning of enzymes, antibodies, receptors, and signaling molecules. Ultimately, the design of biomaterials will include this molecular recognition ability, whether it is a smart system that recognizes only diseased cells, an implantable device with a tailored surface that does not elicit an immune response, or a sensor that can track levels of a specific compound in situ. In addition to use as biomaterials, the creation of synthetic materials with recognitive abilities will have great benefits in the areas of separations, assays, catalysis, and mass transport.

Synthetic Systems for Molecular Recognition. Undoubtedly, methods for the creation of materials with recognitive abilities similar to those shown in biological molecules such as enzymes and antibodies have been heavily sought after.

Molecular Recognition with Crosslinked Networks. By crosslinking the polymer chains, it is possible to restrict the number of conformations a given chain may adopt. In the formation of a configurationally biomimetic imprinted polymer (CBIP), interactions between a template molecule and the monomer feed molecules leads to the creation of a binding site that is subsequently locked in by polymerization and crosslinking. To date, imprinted structures have been successfully used in chromatographic applications [34-39], as sensors [40-42], and even as catalytic elements [43-46].

Wulff, et al. [34] demonstrated the first simple molecularly imprinted polymers (MIPs) utilizing monomers that had been covalently linked to the functional monomers in order to establish a proper 1:1 stoichiometric ratio. After polymerization, the template molecule was freed through lysis. This covalent technique of imprinting has several advantages including efficient use of all available functional groups and a propensity to form a more uniform binding pocket, but is restrictive in what monomers may be used. A technique later pioneered in the laboratories of Mosbach involves imprinting a freely soluble template without the use of covalent linkages [47, 48]. This technique allows for greater flexibility in the choice of functional monomers as well as template molecule.

However, reaction conditions need to be more strictly controlled to maximize interaction between template and monomer molecules. In addition, a number of different binding sites may form leading to some nonspecific binding.

The molecular imprinting procedure. The production of a successfully imprinted polymer results in a material with recognitive properties. While many polymerization techniques are amenable to the imprinting procedure, most utilize a free radical technique with either thermal, ultraviolet, or redox methods providing the initiating radicals [49]. Common monomers include the methacrylate and acrylate family of molecules, acrylamides, and other vinyl derivatives as these are readily available, polymerize easily with the free radical technique, and are available with a number of functional groups [50]. In addition to monomer molecules with an array of functional groups, it is crucial to have crosslinking agents that incorporate well into the polymerization. Usually, a crosslinking agent is selected such that it has similar reactivity to the monomers used so as to form a network uniform in crosslinking density [51].

The prepolymerization mixture includes the functional monomers, crosslinking agent, initiating species, template, and solvent if desired. As free radical polymerizations are sensitive to the presence of radical scavengers such as dissolved oxygen, the mixture is first purged with an inert gas such as nitrogen. Polymerization is then initiated. As suggested by Pande et al. [28] in their work on random heteropolymers, successful imprinting is more likely to occur at lower temperatures since entropic effects are lessened, which suggests the use of either a redox or UV initiation method. However, many groups have successfully used thermal initiation, albeit at lower temperatures than normally seen for thermal polymerizations.

Following polymerization, the imprinted polymer is swollen in solvent to facilitate the removal of the template molecule. Often times before dialysis, the crosslinked material is crushed and sieved to produce particles of a given diameter in order to facilitate mass transfer. Once free of template, the MIPs are subjected to analysis of their binding ability through a variety of techniques including liquid chromatography, NMR, and microcalorimetry.

Yu and Mosbach [35] studied the influence of crosslinking density on the recognitive ability of a non-covalently formed MIP imprinted for the separation of Boc-D-Trp and Boc-L-Trp enantiomers. In their studies, it was shown that the ability to separate enantiomers decreases as the crosslinking density is decreased. This supports work done by Wulff, et al. [52] with covalently imprinted materials where in addition to a decrease in recognition, there was also a minimum amount of crosslinking needed for recognition. While increases in crosslinking density are favorable to the recognitive ability of a MIP, the resultant decrease in network mesh size may act to hinder diffusion through the network, especially limiting for the recognition of large molecules such as proteins.

Applications of molecularly imprinted materials. Historically, the main application of MIPs has been in chromatographic uses. Crosslinked recognitive materials are formed with through the imprinting process and are then crushed into particles suitable for packing into chromatographic columns [49], or used in thin layer chromatography [37]. The recognitive ability of the particles allows for affinity chromatography whereby only the compound of interest is bound by the column and all other species elute freely. This has worked especially well for the separation of enantiomers, a classically difficult separation. In 1974, Wulff, et al., [34] first suggested the formation of configurationally biomimetic imprinted polymers for the separation of D,L-glyceric acid. Since then, a significant amount of work has been focused on creating MIPs for separations, including enantiomers of Tryptophan derivatives by Yu and Mosbach [35], nicotine-like compounds by Andersson et al. [36], D- and L-phenylalinine anilide by Kriz et al. [37], penicllin G and related compounds by Cederfur et al. [38], and amino acids by Kempe and Mosbach [39].

More recently, MIPs have been employed as sensing elements due to their molecular recognition abilities. Due to the minute amounts typically bound, a highly sensitive quartz crystal microbalance (QCM) is used to determine the mass of analyte absorbed. Detection by QCM has been used by Haupt et al. [40] for the detection of R- and S-propanolol hydrochlorides, by Liang et al. [41] for the detection of epinephrine, and by Hilt et al. [42] for the detection of D-glucose.

Traditionally, the design of biomaterials has focused on biocompatibility—the propensity for a material to not invoke a foreign body response upon implantation or contact in the body. Numerous studies have been done to tailor surface properties so as to not elicit an immune response. The main method has been to functionalize the surface with a hydrophilic molecule, such as grafted poly(ethylene glycol) chains, to mask the foreign surface from protein adsorption. However, it is now being recognized that molecular recognition may play an important role in future biomaterials design. Materials that show good biocompatibility are being further enhanced to include molecular recognition. Articles by Ratner [53] and by Peppas and Langer [54] discuss how building recognitive abilities into biomaterials has the potential to radically advance the field. Potential applications include: (1) materials that invoke healing pathways to rebuild tissue in the implantation area; (2) combined sensing element/controlled release device to meter and release appropriate amounts of therapeutic compounds; (3) recognitive materials specific to toxins or deleterious signaling molecules (such as angiotensin) for rapid detoxification in the blood stream; and (4) antibody or enzyme mimics for in vivo use from synthetic materials.

Researchers working towards these goals have focused on the creation of materials that are suitable for use in the body yet interact with the biomolecule of interest. Byrne et al. [55, 56] and used an imprinting technique to create hydrogels capable of binding D-glucose. This technique was later coupled with sensing technologies developed by Hilt et al. [57] to form a microsensor capable of detecting D-glucose [42]. Other glucose responsive materials have been formed by Oral and Peppas [58] utilizing star polymers and by Parmpi and Kofinas [59]. In addition to small biomolecules, Bolisay et al. prepared a configurationally biomimetic imprinted material suitable for the detection and screening of baculoviruses [60]. Molecular imprinting is well-known and can be conducted using one or more biomolecules, e.g., Acetaldehyde (metabolism byproduct); Adenine, adenosine 5V-triphosphate (ATP); Amino acid and peptide derivatives: Z-L-Tyr-OH; Z-L-Phe-OH; Z-DL-Phe-OH; Z-L-Glu-OH; Boc-L-Phe-Gly-Oet; Z-L-Ala-L-Ala-OMe; Z-L-Ala-Gly-L-Phe-OMe; Z-L-Phe-OH; Ampicillin (penicillin antibiotic); a-Amylase (enzyme); Angiotensin II (SA) (competitive inhibitor of, peptide hormone angiotensin II); Bupivacaine (anaesthetic drug); Butein (active anti-EGFR inhibitor); Caffeine (stimulant drug); Cephalexin (antibiotic drug; in a-aminocephalosporins class); Chlorphenamine (anti-histamine drug); Clenbuterol (h adrenergic blocker); Cortisone (steroid); Creatine (metabolite); Creatinine (metabolite); Cholesterol (steroid); Cholic acid sodium salt (bile acid); Carbohydrates: glucose; lactose; maltose, glucose; Glucose; Maltose; lactose; cellobiose; Carbohydrate derivatives: octyl-glucoside; p-nitrophenyl fucoside, p-nitrophenyl galactoside; Peracetylated phenyl a- and h-D-galactosides; Diazepam (i.e., valium, benzodiazepine anxiolytic drug); Enkephalin (neuropeptide); Ephedrine (stimulant drug); Epinephrine (adrenaline hormone); Estradiol (estrogenic steroid hormone); Ethynylestradiol (estrogenic steroid hormone derivative); 9-ethyladenine (nucleotide base derivative); 9-ethyladenine acetate (nucleotide base derivative); Glucose oxidase (enzyme); L-glutamine (amino acid); Histidine (N-terminal) dipeptides; Homocysteine (non-essential amino acid); Horseradish peroxidase (enzyme); Ibuprofen (non-steroidal anti-inflammatory drug); Ketoprofen (non-steroidal anti-inflammatory drug); Lysozyme (enzyme); Morphine (narcotic analgesic drug); Naproxen (non-steroidal anti-inflammatory drug); Nerve agent degradation products; (S)-nilvadipine (dihydropyridine calcium antagonists); Nucleoside base derivatives: tri-O-acetyl adenosine; tri-O-acetyl guanosine; di-O-acetyl thymidine; tri-O-acetyl cytidine; tri-O-acetyl uridine; Nucleotide base derivatives: 9-ethyladenine; 1-propyl thymine; 1-propyl cytosine; 1-cyclohexyl uracil; Oxytocin (hormone); Paracetamol (i.e., acetaminophen, analgesic); Phenylalanine (amino acid); (E)-piceatannol (active anti-EGFR inhibitor); Propanolol (h adrenergic antagonist); Quercetin (active anti-EGFR inhibitor); Ribonuclease A (enzyme); Ricin A and B Chains (toxin bean lectin); (S)-ropivacaine (anaesthetic); Scopolamine (anti-cholinergic, anti-infective; and analgesic alkaloid drug); Sulfonamides (antibiotic drug); Testosterone (steroid hormone); Tetracycline (antibiotic drug); Theophylline (Bronchodilator drug); Timolol (h adrenergic blocker); Trypsin (enzyme); Tyrosine (amino acid); Tyr-Pro-Leu-Gly-NH2 (tetrapeptide); Leu-enkephalin; Leu-enkephalin; Morphine; Morphine; Ampicillin; S-propranolol; D-phenylalanine; Adenine; 9-ethyladenine; 9-ethyladenine; 9-ethyladenine acetate; Cholesterol; Homocysteine; Trypsin; Theophylline; see, e.g., Hilt & Byne, Configurational biomimesis in drug delivery: molecular imprinting of biologically significant molecule, Advanced Drug Delivery Reviews 56 (2004) 1599-1620, relevant portions and citations incorporated herein by reference.

Protein Imprinting. The potential applications for a recognitive material capable of binding a protein are numerous, including diagnostic devices for protein assays, systems for use in immunochemistry, and separation media for extremely complicated protein mixtures. Production of such materials, however, is difficult for several reasons. First, it is known that the presence of water reduces the interactions between template and monomer since the water molecules compete for hydrogen bonds [33]. Most imprinting, therefore, is done in the presence of non-aqueous media. However, peptides and proteins are especially sensitive to differing solvent conditions and may denature in harsh solvents. Secondly, the large diameter of protein molecules may preclude the use of a densely crosslinked polymeric network since the mesh size of the network is too small to allow for efficient diffusion. It is also unclear how selective a protein imprinted material can be made, and whether subtle changes, such as the process of site directed mutagenesis, can be differentiated by these materials.

To date, several attempts have been made at creating MIPs for the recognition of oligopeptides and proteins. Shnek et al. [61] and Kempe et al. [62] focused on a surface imprinting approach whereby monomers capable of complexing a metal ion were polymerized into a MIP for with an affinity for proteins with surface exposed histidine residues. Polymers imprinted in the bulk have been prepared for the recognition of peptides by Andersson et al [63] and for the recognition of proteins by Venton and Gudipati [64]. Recently, Rachkov and Minoura [65] have demonstrated a method where only a fragment of the protein is used in the imprinting process, leading to a site that is favorable for a portion of the whole protein. This so called "epitope approach" mimics the ability of antibody molecules to recognize a portion of a protein structure.

Essential oils. Essential oils are complex mixtures of numerous compounds, they are aromatic oily liquid and can be extracted from various parts of the plants. Some of the main chemical groups found in essential oils include alcohols, aldehydes, esters, ethers, ketones, phenols and terpenes. Their use is mostly related to food as flavoring, to perfumes as fragrances and to pharmaceuticals for their functional properties. To date they are widely used as air freshener, several patents are reported dealing with their applications as deodorant, some are related to their use as good smelling insect repellent. As reported in the review proposed by Burt (2004), antimicrobial properties of some essential oils have long been recognized; in particular they have been shown to exhibit antiviral, antimycotic, antitoxigenic, antiparasitic and insecticidal properties. In the literature several works reports on their use to improve the shelf-life and safety of food and packaged food.

Controlled release systems. As reported by Peppas and Am Ende (1997), the incorporation of fragrances in polymers for the purpose of controlled release over a period of 12 or more hours has been studied. Incorporation of essential oils in polymers could lead to new and innovative products for prolonged delivery of these compounds. Peppas and Brannon-Peppas (1996) provided a wide view on papers dealing with the use of systems in which the fragrances are released from different matrices. In addition to those one, the release of linalool and linalyl acetate (the major components of aromatic lavender essential oils) from biopolymer gliadin-based nanoparticles (Duclairoir et al., 2002), the release of eucalyptus essential oil from alginate complex capsule (Chang and Dobashi, 2003) and the release of limonene from polysaccharides matrices (Secourad et al., 2003) were studied. Besides, Nakayama et al. (2003) studied the release of orange essential oils from temperature responsive membranes obtained by UV polymerization of mixture of N-isopropyl acrylamide and Polyethyleneglycole dimethacrylate. These references provide interesting information on the fragrance release mechanism but, due to the requirements and characteristics of essential oils, swelling-controlled release systems are highly desirable devices for such applications, relevant portions incorporated herein by reference.

The preparation of the above mentioned devices requires the understanding of the thermodynamic of the three-components system, consisting of the polymer, the fragrance and the liquid which is usually in contact with the device. The release of a fragrance initially embedded into the polymer matrix into the surrounding solvent is limited by several factors: the initial amount of fragrance loaded into the polymer, the solubility of the fragrance in the solvent, the equilibrium partition coefficient of the fragrance between polymer and solvent and the diffusional barrier.

The present disclosure generally relates to biomimetic polymer network compositions, methods of forming such polymer compositions, and methods of using such compositions. These compositions and have improved properties that make them useful for a variety of applications; in particular, the loading and delivery of therapeutic agents.

The biomimetic polymer networks of the present disclosure generally include a polymer network having architectures that have selective affinity for a moiety. Such biomimetic polymer networks may have shape specific cavities that match the moiety, as well as chemical groups oriented to form multiple complexation points with the moiety. In terms of selectivity, the resulting polymer networks are selective due to the particular chemistry of the binding site, the orientation and stabilization of the chemistry in a crosslinked matrix, as well as by the size and shape of the site for the template biomolecule.

In some embodiments, the biomimetic polymer networks may further comprise a moiety. Such compositions may be capable of releasing the moiety in a relatively controlled fashion. The moiety may be present on a target compound, for example, a therapeutic agent. Accordingly, the compositions and methods of the present disclosure may be used in the treatment of a disease. For example, the compositions of the present disclosure may be used as a vehicle to deliver a therapeutic agent to a subject (e.g., a human) in need thereof. The compositions of the present disclosure also may be used to form a medical device or an article. The present disclosure also provides methods of forming a biomimetic polymer network of the present disclosure.

The moiety may be any portion of a molecule recognized by a biomimetic polymer network of the present disclosure. The moiety may be covalently bound to a target compound, for example, a therapeutic agent. In this way, the moiety may be used to associate a target compound with a biomimetic polymer network of the present disclosure. The moiety should either already be present on the target compound or capable of being conjugated to a target compound. Conjugation of moieties to therapeutic agents is known in the art, for example, as disclosed in A. Wong and I. Toth, *Curr. Med. Chem.* 8:1123-36 (2001), the relevant disclosure of which is incorporated by reference. Examples of suitable moieties include, but are not limited, to sugars (e.g., glucose), carbohydrates, peptides, and functional groups. A specific example of a therapeutic agent that comprises a moiety is streptozotocin (R. R. Herr, et al., *J. Am. Chem. Soc.* 89:4808-09 (1967)), which has a glucose moiety.

In certain embodiments, the moiety is a sugar. For example, the sugar may be a monosaccharide. Monosaccharides have the chemical formula $(CH_2O)_n$ and the chemical structure $H(CHOH)_nC=O(CHOH)_mH$. If n or m is zero, it is an aldose, otherwise it is a ketose. Monosaccharides may include aldoses, trioses (e.g., glyceraldehyde), tetroses (e.g., threose), pentoses (e.g., ribose, xylose), hexoses (e.g. glucose, fructose, mannose, galactose), ketoses, trioses, tetroses, pentoses (e.g., ribulose), hexoses (e.g., fructose). Any of the L and D isomers of a sugar also may be used, although the D isomer may be more preferred for biological applications. Other examples of suitable sugars include polysaccharides. Polysaccharides have a general formula of $C_n(H_2O)_{n-1}$ where n is usually a large number up to 500. Disaccharides, such as, for example, sucrose, lactose, maltose, and the like may be used. Yet another example of suitable sugars includes oligosaccharides and low molecular weight carbohydrates (e.g., having a molecular weight no greater than about 2,000 Da). Further, each carbon atom that supports a —OH group (except for the first and last) is chiral, giving rise to a number of isomeric forms all with the same chemical formula.

Specific embodiments may use the following monosaccharides as moieties: monoses, dioses, trioses, tetroses, pentoses, aldo-pentoses, including arabinose, ribose, deoxyribose and xylose, keto-pentoses including ribulose, hexoses including aldo-hexoses such as: allose, altrose, galactose, glucose, mannose and talose, and keto-hexoses such as fructose, heptoses including keto-heptoses such as mannoheptulose and sedoheptulose, octoses such as octolose, 2-keto-3-deoxy-manno-octonateand and nonoses such as sialic acid.

Specific embodiments may use mucopolysaccharides. Mucopolysaccharides are long unbranched polysaccharides consisting of a repeating disaccharide unit. This unit consists of an N-acetyl-hexosamine and a hexose or hexuronic acid, either or both of which may be sulfated. Members of this family vary in the type of hexosamine, hexose or hexuronic acid unit they contain e.g. glucuronic acid, iduronic acid, galactose, galactosamine, and glucosamine. They also vary in the geometry of the glycosidic linkage. Specific example polysaccharides that may be used as moieties include: chondroitin sulphate, dermatan sulphate, keratan sulphate, heparan sulphate, heparin, sodium heparin, hyaluronic acid and hyaluronan.

In other embodiments, the moiety may be a lipid or a short amino acid sequence (e.g., a sequence of about twenty amino acids in length). In particular, lectins may be used as a moiety. Lectins are carbohydrate-binding proteins involved in a variety of recognition processes and exhibit considerable structural diversity. A large variability in quaternary association resulting from small alterations in essentially the same tertiary structure is a property exhibited specially by legume lectins. The strategies used by lectins to generate carbohydrate specificity include the extensive use of water bridges, post-translational modification and oligomerization. Other carbohydrate-based structures may be used as moieties may be located at http://www.chem.qmul.ac.uk/iupac/2carb/ (accessed Apr. 27, 2006), incorporated by reference herein.

In general, the compositions of the present disclosure have enhanced affinities (e.g., impart greater affinity, bound ratios greater than 1) for a chosen moiety, among other things, allowing for increased loading efficiency. Accordingly, the compositions of the present disclosure also may be used to increase the loading of a target compound or control the release rate of a target compound or both. The compositions of the present disclosure also may be used for delivery of a therapeutic agent. For example, the compositions of the present disclosure may be used as an excipient or as a vehicle for a therapeutic agent. Specifically, higher quantities of a therapeutic agent having a moiety can be loaded within the biomimetic polymer networks of the present disclosure, therefore enabling for higher doses to be loaded. The release of a moiety may be tailored to give a desired release profile, for example, for sustained release of a therapeutic agent. Thus, when the moiety is bound to a therapeutic agent, treatment with the therapeutic agent may be optimized.

The compositions of the present disclosure may be formed using configurational biomimetic imprinting. Configuration biomimetic imprinting techniques generally involve forming a prepolymerization complex between the template molecule (e.g., a moiety) and functional monomers or functional oligomers (or polymers) with specific chemical structures designed to interact with the template either by covalent chemistry or noncovalent chemistry (self-assembly) or both. Once the prepolymerization complex is formed, the polymerization reaction occurs in the presence of a crosslinking monomer and an appropriate solvent, which controls the overall polymer morphology and macroporous structure. Once the template is removed, the product is a heteropolymer network with specific recognition elements for the template molecule.

The network structure depends upon the type of monomer chemistry (i.e., anionic, cationic, neutral, amphiphilic), the association strength and number of interactions between the monomers and template molecule, the association interactions between monomers and pendent groups, the solvent type and the amount of solvent in the mixture, the reactivity ratios of the monomers, and the relative amounts of reacted monomer species in the structure. Since noncovalent forces are weaker than covalent bonds, an increased number of interactions are needed for stable binding and recognition. On a per-bond basis, noncovalent bonds are 1-3 orders of magnitude weaker. Therefore, a greater number of noncovalent bonding with matching structural orientation is needed for aqueous recognition.

A wide variety of polymers may be used to form the heteropolymer network. These include polymers produced by reaction of acrylamides and all their substituted structures including: methacrylamide, ethacrylamide, isopropyl acrylamide, etc., acrylic acid, methacrylic acid, ethacrylic acid, all alkyl acrylic acids, any dicarboxylic acid, such as crotonic acid, phthalic and terephthalic acid any tricarboxylic acid with itself another monomer of the above list (forming a copolymer), two other monomers from the above list (forming terpolymers), or three or more monomers from the above list forming higher order coploymers. The above may be in linear, branched or grafted form, the grafted chains being exclusively one polymer or copolymers of the above, ionically bound or complexed by hydrogen bonds.

The above may be crosslinked in the presence of crosslinking agents to form insoluble but swellable gels or networks, having the ability to absorb water, physiological fluids, buffers or salt solutions with final swelling as low as 1 weight % of water and as high as 99.9% water.

The above crosslinking may be achieved with ethylene glycol dimethacrylate, ethylene glycol diacrylate, ethylene glycol trimethacrylate, ethylene glycol diacrylate, ethylene glycol multi methacrylate where "multi" stands for n=4 to 200 units ethylene glycol multi acrylate where "multi" stands for n=4 to 200 units same as above but propylene glycol multi methacrylate where "multi" stands for n=1 to 200 units same as above but alkylene glycol multi methacrylate where "multi" stands for n=1 to 200 units. One may also use higher order acrylates and methacrylates including but not limited to 1,1,1 trimethylolethane trimethacrylate (TrMETrMA, Molecular Weight 324.4); 1,1,1 trimethylolpropane triacrylate (TrMPTrA, Molecular Weight 296.3); 1,1,1 trimethylolpropane trimethacrylate (TrMPTrMA, Molecular Weight 338.4); pentaerythritol triacrylate (PETrA, Molecular Weight 298.3); glycerol propoxy triacrylate (GlyPTrA, Molecular Weight 428.5); pentaerythritol tetraacrylate (PETeA, Molecular Weight 353.2); ethoxylated 1,1,1 trimethylolpropane triacrylate (ETrMPTrA, Molecular Weight 428); glycerol propoxylated triacrylate (GlyPTrA, Molecular Weight 428) and glycerol trimethacrylate (GlyTrMA, Molecular Weight 396.3). One may also use with "star polymers" or "dendrimers" with up to 72 independent chains ending in acrylates or methacrylates.

The initiator may be IRGACURE® products of the Ciba Geigy company including IRGACURE 184, IRGACURE® 379, Ciba® IRGACURE® 819, and Ciba® IRGACURE® 250. Any other photoinitiator may also be used. The initiator may also be any peroxide including but not limited to benzoyl peroxide, cumyl peroxide, etc. or Azobis isobutyronitrile.

In some embodiments, the biomimetic polymer network of the present disclosure may be formed using a template molecule (e.g., D-glucose) and functional monomers selected to match corresponding template molecule (e.g., glucose binding protein residues, such as aspartate, glutamate, and asparagines, as well as biological mechanisms of action that involve recognition The template molecule may be added in stoichiometric amounts in regard to the functionality of the template molecule. Since solvent interaction can stabilize or destabilize binding in noncovalent systems, functional monomers may be selected based on optimizing specific noncovalent, self-assembly interactions (hydrogen bonding) with the template molecule within an aprotic solvent (e.g., dimethylsulfoxide). Such techniques are generally applicable to template molecules, in which hydrogen bonding, hydrophobic, or ionic contributions will direct recognition of the moiety. The formation of an exemplary biomimetic polymer network of the present disclosure according to the methods of the present disclosure is described below.

The multilayered mimetic structures may be constructed from a variety of coating processes, including pan coating, air-suspension coating, centrifugal extrusion, vibrational nozzle coating, supercritical fluid (SCF) based processing, fluidization (both conventional Wurster coaters such as the Glatt device) and rotating, or spray-drying.

Figure 2:
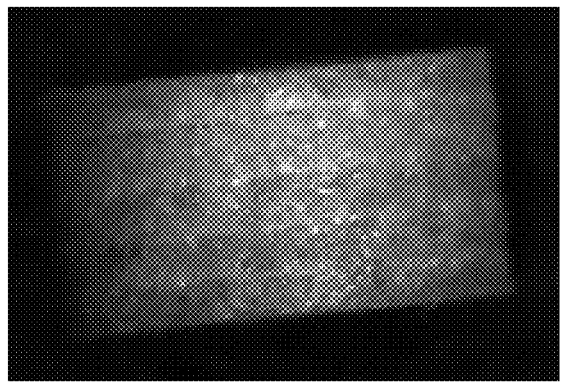
FIG. 2. A 9-layer tablet: 5 recognitive layers with 4 bovine serum albumin layers in between. Note the distinct, lighter color where the BSA layers are and the different noticeable particles.

The multilayered mimetic structures shown in FIGS. 1-2 may be constructed using a Grow Max spouted bed assisted with a draft tube and a bottom spray, also known as the Wurster configuration. The height of the bed is 535 mm and the diameter of the bed is 160 mm at the bottom and 300 mm at the top.

The bed is equipped with a sampling port to allow the microcapsule to be withdrawn and analyzed during the coating process. The bed is also equipped with a viewing window to allow the observation of the fluidizing microcapsule during the coating process. The length of the draft tube to be used is preferably 200 mm and is located 15 mm above the air distributor. The diameter of the draft tube is 70 mm. The pneumatic spray nozzle with a liquid caliber of 1.0 mm can be used to atomize the dispersion fed to the bed. A bag filter with 5 µm opening can be used to prevent the microcapsules from escaping through the top of the bed. The bag filter must be shaken frequently to prevent the microcapsule from adhering to the bag filter. The schematic diagram of the Wurster bed apparatus is shown in FIG. 2.

The advantages of the Wurster process compared to conventional fluidized bed process are: (i) the high inertia introduced in the Wurster process to circulate the particles prevents the agglomeration of the particles and (ii) the recycling profile creates a uniform coat around the particles. The circulating pattern of the particles inside a Wurster bed is made possible by a draft tube. The air inlet is concentrated just under the draft tube. This creates a high air velocity inside the draft tube and a vacuum like effect at the base of the draft tube. The particles collected under the bed are readily pulled by the air inlet into the draft tube and being carried to the top of the bed. At the exit of the draft tube, there is a sudden expansion, from the diameter of the draft tube to the diameter of the chamber. This expansion causes the particle to lose its velocity gradually and finally gravity will pull the particles back down along the wall of the chamber to the base and the process will be repeated.

Generally, a Wurster bed is equipped with a bottom spray, and hence, every time the particles pass through the based of the draft tube, latex dispersion will be sprayed on the particles. This process repeats every time the particles pass through the bottom of the draft tube, and finally, a uniform coating can be obtained. The ability to coat such small particles uniformly has broadened the applications of the Wurster process for particulate drug delivery systems.

The Wurster coating process employed in the present disclosure is very versatile and can be applied for many different materials. The process has been shown to work for many different type of cores including calcium carbonate crystal, glass beads and lactose [1-6]. Many latex dispersions have also been shown to be able to be coated using this process, such as poly(ethyl acrylate/methyl methacrylate/2-hydroxyethyl methacrylate) (P(EA/MMA/HEMA)), composite latex of core P(EA/MMA/HEMA) and P(NIPAAm) shell, crosslinked P(NIPAAm), Eudragit RS30D, L30D-55 and FS30D, and ethyl cellulose [1-6].

The Wurster coating process is a very harsh process. The process involves exposure to high temperature and high shear stress. The process requires high temperature to dry the coated microcapsules. The high shear stress is required to atomize the latex dispersion before being sprayed on the circulating microcapsules. Fortunately, the MIP nanoparticles have shown promising stability at high temperatures and high shear stresses.

One problem encountered with the coating process is the formation of a "snowman-like" structure due to agglomeration. These structures are produced by the fusion of two microcapsules. This fused structure creates weak spot along the contact point of the two microcapsules. Agglomeration prevents the formation of a single core microcapsule, which is the structure desired in this work. Several factors that affect the degree of agglomeration using the Wurster bed include: the feed rate of the latex dispersion, the flow rate of the dried air to fluidize the microcapsule and the temperature of the inlet air, the outlet air and the bed and the like.

As used herein, the term "recognitive polymer" refers to a network structure of polymeric layers that swell to release active agents within the polymer based on a number of factors, including: the type of monomer chemistry (i.e., anionic, cationic, neutral, amphiphilic), the association strength and number of interactions between the monomers and template or recognitive molecule used at the time that the polymer is formed, the association interactions between monomers and pendent groups, the solvent type and the amount of solvent in the mixture, the reactivity ratios of the monomers, and the relative amounts of reacted monomer species in the structure. Since noncovalent forces are weaker than covalent bonds, an increased number of interactions are needed for stable binding and recognition. On a per-bond basis, noncovalent bonds are 1-3 orders of magnitude weaker. Therefore, a greater number of noncovalent bonding with matching structural orientation is needed for aqueous recognition.

In the present invention, the multi-layer tablet includes a "swelling front" that separates the rubbery region (region of swollen CBIP/HPMC with enough water to have its $T_g$ below the experimental temperature) and the "glassy" region (region where the CBIP/HPMC has a $T_g$ above the experimental temperature).

A wide variety of polymers may be used to form multilayered structures. These include polymers produced by reaction of acrylamides and all their substituted structures including: methacrylamide, ethacrylamide, isopropyl acrylamide, etc., acrylic acid, methacrylic acid, ethacrylic acid, all alkyl acrylic acids, any dicarboxylic acid, such as crotonic acid, phthalic and terephthalic acid any tricarboxylic acid with itself another monomer of the above list (forming a copolymer), two other monomers from the above list (forming terpolymers), or three or more monomers from the above list forming higher order copolymers. The above may be in linear, branched or grafted form, the grafted chains being exclusively one polymer or copolymers of the above, ionically bound or complexed by hydrogen bonds. For application in organisms, such as humans, the polymers that will have most application are those that are biocompatible, and in some cases, also biodegradable.

EXAMPLE 1

Recognitive/responsive tablet systems. Recognitive systems that show diffusional times that are much shorter than for films were development by using multilayered tablets produced from recognitive particles that had been compressed by "standard" pharmaceutical techniques. Swelling of hydrophilic polymeric tablets has been the subject of significant research in the last few years. Of particular interest are studies on the swelling and subsequent dissolution of hydroxypropyl methyl cellulose (HPMC) tablets.

Molecularly, individual chains absorb water so that their end-to-end distance and radius of gyration expand to the new solvated state. This expansion (swelling) is observed macroscopically by the formation of distinct fronts separating unswollen and swollen regions. In the macroscopic observation of the swelling process we have identified a "swelling front" which clearly separates the rubbery region (region of swollen CBIP/HPMC with enough water to have its Tg below the experimental temperature) and the glassy region (region where the CBIP/HPMC has a Tg above the experimental temperature). A second front is the "erosion front" which separates the matrix from the solvent (glucose solution or water).

The rupture lines due to the recognition process as well as the gel layer formed on the glassy core of a swellable matrix are considered to be controlling elements of drug release kinetics, although other mechanisms may be functional in such systems. The gel layer structure changes during tablet swelling, due to the molecular extension of the solvated polymeric chains. The diffusion front position in the gel phase during drug release is usually dependent on drug solubility and loading. In fact, the diffusion front movement can be related to drug dissolution rate.

Preparation of Particles from Recognitive Polymers. The typical procedure of creating the particles from recognitive polymers includes MAA crosslinked with EGDMA around D-glucose, combined with deionized water, ethanol, and DMPA. Generally, the percentages were—MAA: 3.25 wt %, D-glucose: 1.5 wt %, DI water: 31 wt %, Ethanol: 36 wt %, EGDMA: 28 wt %, DMPA: <1 wt %. Some solutions contained more ethanol or less EGDMA in order to obtain a more continuous film.

After the recognitive films were polymerized for 30 minutes in the UV lamp box, they were washed in deionized water (DI water) for 24-48 hours on average. Once taken out of the water, the films were placed in ventilated containers (two weigh-boats taped together with holes along top) and placed in a vacuum oven set at 30 C for at least 24 hours. After the films were completely dry, they were taken out of the oven and then crushed using a mortar and pestle until a very fine powder was produced; the goal was to try and get all the crushed particles to be the same size (roughly 100 micrometers).

Preparation of Control Samples. All control samples were prepared the exact same way as recognitive polymers, except without adding D-glucose to the monomer solution. The same procedures were used minus the D-glucose amounts.

Preparation of Tablets by Compression. There were various procedures for forming the mixture used in tablet compression. The first few procedures did not form durable, lasting tablets because the amounts of binders and fillers were too small or were not in the correct ratio. However, once a procedure produced tablets that remained intact, similar formulas and methods were used.

According to the first protocol developed, reliable tablets were produced using 53.9 wt % CBIP microparticles, 10.9 wt % microcrystalline cellulose, 34.4 wt % Poly(N-vinyl-2-pyrrolidone) (PNVP) K-25, a binder, and less than 1 wt % magnesium stearate, a lubricant (Table 1). The total weight was 582 milligrams. First, the microparticles of recognitive polymers were weighed and mixed with microcrystalline cellulose in a weigh-boat using a spatula. A solution of 20% PNVP was made by combining 4 mg PNVP in 20 ml deionized water. A sample of 1 ml of 20% PNVP solution was added to weigh-boat drop-by-drop using a 1000-ml micropipette. The mixture was then stirred with the spatula and placed on a hotplate at a very low temperature to allow liquid to evaporate. Before the mixture was completely dry, it was pushed through a metal sieve into granules. These granules were then placed in a ventilated container in a vacuum oven to completely dry. Once the granules were completely dry, the magnesium stearate was added to the mixture and stirred with a spatula to get a homogenous mixture. This microparticle mixture was then weighed into 20-23 mg samples that would be the recognitive layers of each tablet. Bovine serum albumin was weighed into 5-6 mg samples to be used in between the recognitive layers (instead of insulin).

The tablets were compressed using a Corning tablet press and a 6.33 mm diameter punch with flat edges; the pressure was 6000 N/inch. The first recognitive layer was a 20-23 mg sample of microparticle mixture placed inside the lower punch area and compressed; it was then left in the bottom as the additional layers were added. A 5-6 mg sample of bovine serum albumin (BSA) was then poured on top of this first recognitive layer. A smaller punch was used lightly with a hand to even out this layer so it is as flat as possible. It was then compressed with the top punch so that both layers become one unit. This procedure was repeated until 5 recognitive layers and 4 BSA layers were pressed all together (creating a 9-layer tablet).

Similar mixtures were made in smaller amounts using 66.0 wt % microparticles, 5.9 wt % cellulose microcrystalline, 27.3 wt % PNVP K-25, and <1 wt % magnesium stearate (Table 2). Another mixture was made using 86.2 wt % microparticles, 12.6 wt % PNVP K-25, and 1 wt % magnesium stearate (Table 3).

From the previous data, a new mixture was made in order to produce thinner tablets without using a wider punch. This mixture included 74.3 wt % recognitive microparticles, 5.0 wt % cellulose microcrystalline, 19.7 wt % PNVP K-25, and <1 wt % Magnesium Stearate (Table 4). The total weight was 405 mg. This mixture followed the same procedures as before, except it was completely dry before pushed through the sieve in order to recover more particles/granules. This time only 7-layer tablets were pressed. In the Bovine Serum Albumin layers, a 1:1 mixture of Bovine Serum Albumin: Hydroxypropylmethylcellulose (HPMC) was used. The recognitive layers were between 10-12 mg and the BSA layers between 5-6 mg.

TABLE 1

Multilayered Tablet Sample No 1.

| | Mass (g) | Percent (%) |
|---|---|---|
| Microparticle | 0.31364 | 53.8771 |
| Cellulose, microcrystalline | 0.06345 | 10.8994 |
| PNVP (K-25) | 0.20000 | 34.3560 |
| Magnesium stearate | 0.00505 | 0.86749 |
| Total Mass (g) | 0.58214 | 100 |

TABLE 2

Multilayered Tablet Sample No 2

| | Mass (g) | Percent (%) |
|---|---|---|
| Microparticles (BLE36) | 0.07970 | 65.9604 |
| Cellulose, microcrystalline | 0.00708 | 5.85947 |
| PNVP (K-25) | 0.03300 | 27.3110 |
| Magnesium stearate | 0.00105 | 0.86898 |
| Total mass | 0.12083 | 100 |

TABLE 3

Multilayered Tablet Sample No 3

| | Mass (g) | Percent (%) |
|---|---|---|
| Microparticles (BLE48) | 0.03428 | 86.17396 |
| PNVP (K-25) | 0.0050 | 12.56913 |
| Magnesium Stearate | 0.0005 | 1.256913 |
| Total mass | 0.03978 | 100 |

TABLE 4

Multilayered Tablet Sample No 4

| | Mass (g) | Percent (%) |
|---|---|---|
| Microparticles | 0.30096 | 74.29644 |
| Cellulose Microcrystalline | 0.02018 | 4.981732 |
| PNVP (K-25) | 0.08 | 19.74919 |
| Magnesium Stearate | 0.00394 | 0.972647 |
| Total mass | 0.40508 | 100 |

Summary of Prepared Samples. The first set of studies produced useful tablets in the form of thick multilayer tablets (minitablets). The total weights and thickness were 134.23 mg, 3.11 mm; 137.2 mg, 3.42 mm; 132.31 mg, 3.4 mm (FIG. 1). For single-layer tablets, the thickness was 0.58 mm, 0.63 mm, 0.68 mm, and 0.65 mm. It was possible to observe the different layers and even particulate aggregates in these tablets (FIG. 2). These tablets were very sturdy and did not break apart when handled. The second and third tablet recipes used higher amount of CBIP microparticles. One recipe without microcrystalline cellulose showed promising results using less of the mixture.

Single-layer tablets made without microcrystalline cellulose were thicker than the others because cellulose has a good compressibility. These tablets crumbled faster than other tablets, possibly because the PNVP was not a sufficient binder to keep all the particles together as one unit.

Figures 3A, 3B:
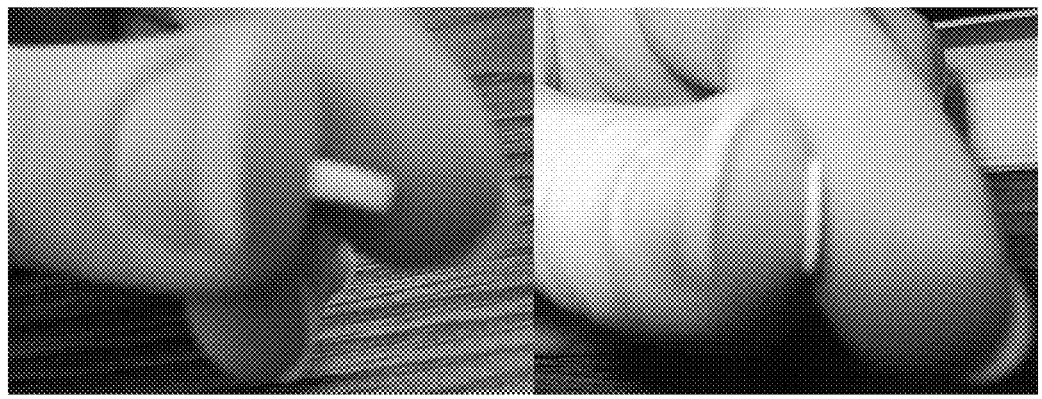
FIGS. 3a and 3b.

The tablet recipe with 5 wt % cellulose and 20 wt % PNVP produced much thinner disks (FIG. 3a). The total weights and thickness were 58.25 mg, 1.55 mm; 59.79 mg, 1.46 mm; 58.47 mg, 1.55 mm; 59.27 mg, 1.63 mm; 60.4 mg, 1.73 mm. For single-layer tablets, the thickness was 0.39 mm and 0.34 mm (FIG. 3b).

Most tablets made from the above recipes were sturdy and did not crumble when handled; only the very thin single-layer tablets seemed to fall apart when stress was applied. They all had a light-brownish hint to them, probably from the PNVP in the mixture. All edges were distinct and made perfect circles from the punch.

Figures 4A, 4B:
FIGS. 4a and 4b.
Figures 5A, 5B:
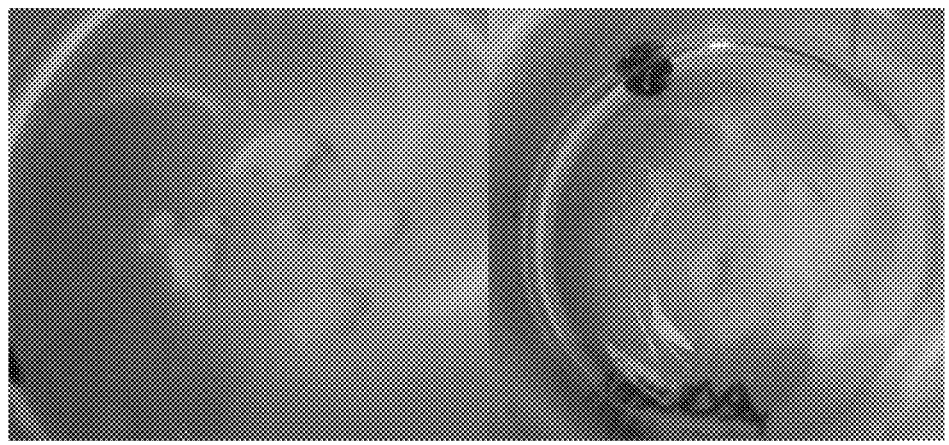
FIGS. 5a and 5b.

Observation of Swelling Process. One set of experiments was run, in which two single-layer tablets with 10 wt % cellulose and 34 wt % PNVP (first recipe) were put into separate beakers, one with DI water and the other with 100 mg/dL D-glucose in DI water. These tablets were both approximately 0.66 mm thick. Both floated on the top of the liquids until rupture and/or swelling. After 20 minutes, the tablets in DI water started crumbling and breaking apart (FIG. 4a). After 30 minutes, the tablets in 100 mg/dL glucose cracked down the middle, but did not crumble and fall to the bottom of the beaker. These tablets were still floating and did not crack significantly more after 60 minutes (FIG. 4b). After 18 hours, both tablets had crumbled and landed in big clumps in the bottom of each beaker (FIGS. 5a and 5b).

Figures 6A, 6B:
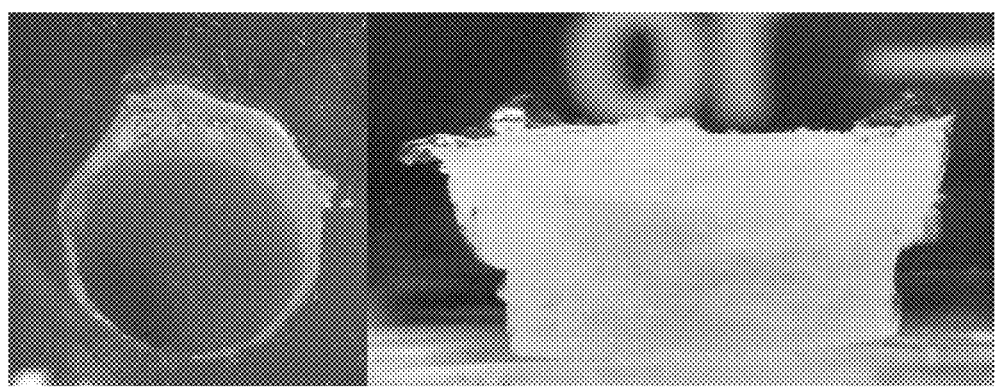
FIGS. 6a and 6b. These photos show the swelling of a 9-layer tablet placed in 100 mg/dL glucose solution. This swelling along the outside was observed starting at 6 min.

Another set of studies used a 9-layer tablet coated with PVA along the lateral area. This tablet was placed in a 50 ml beaker with 40 ml of 100 mg/dL glucose solution. The tablet was dropped into the beaker so that one of the recognitive sides was touching the bottom. After about 6 minutes, the first recognitive layer absorbed glucose and started responding by cracking and swelling along top half began swelling (FIGS. 6a and 6b). Tiny bubbles were observed on the tablet, but it is not clear whether these were from the inside of tablet or formed after the tablet was dropped into the solution. After 13 minutes, a large piece crumbled off the top and landed on the bottom. After several hours, the tablet had disintegrated (FIGS. 7a and 7b). There were little pieces scattered all along the bottom (FIGS. 8a and 8b).

TABLE 5

Below are the data regarding the novel multi-layer recognitive systems:

| Layer | Multilayer Tablet 1 Mass (mg) | Multilayer Tablet 2 Mass (mg) | Multilayer Tablet 3 Mass (mg) |
|---|---|---|---|
| Disk 1 | 21.6 | 23.45 | 22.54 |
| Bovine Albumin 1 | 5.8 | 6.84 | 6.25 |
| Disk 2 | 20.88 | 22.12 | 21.79 |
| Bovine Albumin 2 | 6.26 | 6.03 | 6.56 |
| Disk 3 | 21.74 | 22.7 | 20.67 |
| Bovine Albumin 3 | 6.22 | 6.33 | 5.83 |
| Disk 4 | 22.12 | 21.46 | 21.68 |
| Bovine Albumin 4 | 6.8 | 5.64 | 5.95 |
| Disk 5 | 22.81 | 22.63 | 21.04 |
| Total mass (mg) | 134.23 | 137.2 | 132.31 |
| Thickness (mm) | 3.11 | 3.42 | 3.4 |

TABLE 6

Formula for each disk

| | Mass (g) | Percent |
|---|---|---|
| CBIP microparticle | 0.31364 | 53.87707 |
| cellulose, microcrystalline | 0.06345 | 10.89944 |
| PNVP (K-25) | 0.2 | 34.356 |
| Magnesium Stearate | 0.00505 | 0.867489 |
| Total Mass (g) | 0.58214 | |

TABLE 7

Data for mixture BLE18, A, B, and C.

|  | # moles | % mol (chemicals) | % w/w |
|---|---|---|---|
| Added to A (g) | | | |
| MAA | 0.431 | 0.005008 | 42.18806139 | 3.95790588 |
| D-glucose | 0.1847 | 0.001025 | | 1.69611419 |
| DI water | 4.80038 | 0.266392 | | 44.08225575 |
| ethanol | 4.199847 | 0.091162 | | 38.5675154 |
| EGDMA | 1.235 | 0.006712 | 56.54090759 | 11.34109922 |
| DMPA | 0.03867 | 0.000151 | 1.271031026 | 0.35510956 |
| total mass: | 10.889597 | | | |
| moles: | | 0.011871 | | |
| Added to B (g) | | | |
| MAA | 0.438 | 0.005089 | 27.72581374 | 3.625411552 |
| D-glucose | 0.19095 | 0.00106 | | 1.580530447 |
| DI water | 4.80038 | 0.266392 | | 39.7336829 |
| ethanol | 4.199847 | 0.091162 | | 34.76295396 |
| EGDMA | 2.4129 | 0.013114 | 71.43861612 | 19.9720446 |
| DMPA | 0.03931 | 0.000153 | 0.835570147 | 0.325376548 |
| total mass: | 12.081387 | | | |
| moles chemicals: | | 0.018356 | | |
| Added to C (g) | | | |
| MAA | 0.4236 | 0.004922 | 19.94868158 | 3.19500216 |
| D-glucose | 0.18901 | 0.001049 | | 1.42560755 |
| DI water | 4.80038 | 0.266392 | | 36.20685663 |
| ethanol | 4.199847 | 0.091162 | | 31.67733767 |
| EGDMA | 3.6063 | 0.019599 | 79.43348508 | 27.2005106 |
| DMPA | 0.03907 | 0.000152 | 0.617833338 | 0.294685398 |
| total mass: | 13.258207 | | | |
| moles chemicals: | | 0.024674 | | |

TABLE 8

Data/Recipes for other various mixtures:

|  | Added (g) | Added (ml) | # moles | % mol (chemicals) | % w/w | MW g/mol |
|---|---|---|---|---|---|---|
| BLE4 recipe from 051707 (Zach Hilt's original recipe) | | | | | | |
| MAA | 0.415 | | 0.004822 | 20.03793222 | 3.5511364 | 86.06 |
| D-glucose | 0.1796 | | 0.000997 | | 1.5368291 | 180.16 |
| DI water | 3.992 | 4 | 0.221532 | | 34.159365 | 18.02 |
| ethanol | 3.5505 | 4.5 | 0.077068 | | 30.381469 | 46.07 |
| EGDMA | 3.519 | | 0.019125 | 79.47080132 | 30.111925 | 184 |
| DMPA | 0.0303 | | 0.000118 | 0.491266461 | 0.2592757 | 256.29 |
| total mass: | 11.6864 | | | | | |
| moles chemicals: | | | 0.024065 | | | |
| BLE36 CBIP made 061207 | | | | | | |
| MAA | 0.41635 | | 0.004838 | 20.1081614 | 3.5629108 | |
| D-glucose | 0.18132 | | 0.001006 | | 1.551644 | |
| DI water | 3.992 | 4 | 0.221532 | | 34.161499 | |
| ethanol | 3.5505 | 4.5 | 0.077068 | | 30.383367 | |
| EGDMA | 3.5145 | | 0.019101 | 79.3890966 | 30.075297 | |
| DMPA | 0.031 | | 0.000121 | 0.502741999 | 0.2652822 | |
| total mass: | 11.68567 | | | | | |
| moles chemicals: | | | 0.024059 | | | |
| BLE48 CBIP made 062007 | | | | | | |
| MAA | 0.836 | | 0.009714 | 20.05127152 | 3.5688992 | |
| D-glucose | 0.35971 | | 0.001997 | | 1.5356085 | |
| DI water | 7.984 | 8 | 0.443063 | | 34.083841 | |

TABLE 8-continued

Data/Recipes for other various mixtures:

|  | Added (g) | Added (ml) | # moles | % mol (chemicals) | % w/w | MW g/mol |
|---|---|---|---|---|---|---|
| ethanol | 7.101 | 9 | 0.154135 |  | 30.314298 |  |
| EGDMA | 7.0832 |  | 0.038496 | 79.46001886 | 30.238309 |  |
| DMPA | 0.06068 |  | 0.000237 | 0.488709626 | 0.259044 |  |
| total mass: | 23.42459 |  |  |  |  |  |
|  | moles chemicals: |  | 0.048447 |  |  |  |

Recipe for BLE62 CBIP made 070507

| MAA | 0.4495 |  | 0.005223 | 22.702351 | 3.5544049 |  |
| D-glucose | 0.1898 |  | 0.001054 |  | 1.5008366 |  |
| DI water | 3.992 | 4 | 0.221532 |  | 31.566595 |  |
| ethanol | 4.734 | 6 | 0.102757 |  | 37.433933 |  |
| EGDMA | 3.2499 |  | 0.017663 | 76.77055044 | 25.698466 |  |
| DMPA | 0.03108 |  | 0.000121 | 0.527098559 | 0.245764 |  |
| total mass: | 12.64628 |  |  |  |  |  |
|  | moles chemicals: |  | 0.023007 |  |  |  |

Preparation of Samples. The control samples for these studies with multilaminate systems involved the creation of a 7- or 9-layer "sandwich" similar in composition to the multilayer tablet systems using continuous films or discs (i.e., recognitive layer, followed by the bovine serum albumin, followed by another recognitive layer, etc. . . . ). In this case, however, instead of the recognitive layers, non-imprinted polymer film layers were used (thus preventing any specific recognition of glucose).

Preparation of Multilaminate Systems. The multilaminate systems were developed in the same way as the multilayer tablets, with alternating layers of recognitive film and bovine serum albumin (used in our experiments in the place of a drug such as insulin).

The just-washed polymer films (created using the protocol discussed in Section I of this report) were cut into 8 mm (diameter) circles using a cork borer and were subsequently dried in the vacuum oven. The dried circles were then stacked together (in a dry environment at room temperature) with a layer of bovine albumin serum in between each one (used in our experiment in the place of a drug such as insulin). Once the 7- or 9-layer stack was formed, room temperature vulcanized (RTV) rubber was applied along the circumference of the stack using a toothpick, after which the system was left to dry for at least 24 hours.

Parameters and Layers. The structure of the multilaminate system. In these studies, small amounts of bovine serum albumin were used sufficient to fully cover the discs of the recognitive films below them. FIG. 9 shows a diagram of the several layers of a multilaminate system of the present invention. The amount of BSA/drug to be placed between recognitive layers will depend on the rate of diffusion of water inward and the rate of disintegration of the recognitive layers (among many other things).

The following amounts were used:

TABLE 9

|  | Layer | Amount |
|---|---|---|
| Bottom | Disk 1 | 0.00728 g |
|  | BSA 1 | 0.00061 g |
|  | Disk 2 | 0.00659 g |
|  | BSA 2 | 0.00294 g |
|  | Disk 3 | 0.00626 g |
|  | BSA 3 | 0.00438 g |
|  | Disk 4 | 0.00596 g |

TABLE 9-continued

|  | Layer | Amount |
|---|---|---|
|  | BSA 4 | 0.00512 g |
| Top | Disk 5 | 0.00627 g |

TABLE 10

|  | Layer | Amount |
|---|---|---|
| Bottom | Disk 1 | 0.00502 g |
|  | BSA 1 | 0.00500 g |
|  | Disk 2 | 0.00634 g |
|  | BSA 2 | 0.00504 g |
|  | Disk 3 | 0.00673 g |
|  | BSA 3 | 0.00396 g |
|  | Disk 4 | 0.00679 g |
|  | BSA 4 | 0.00253 g |
| Top | Disk 5 | 0.00659 g |

Figure 10:
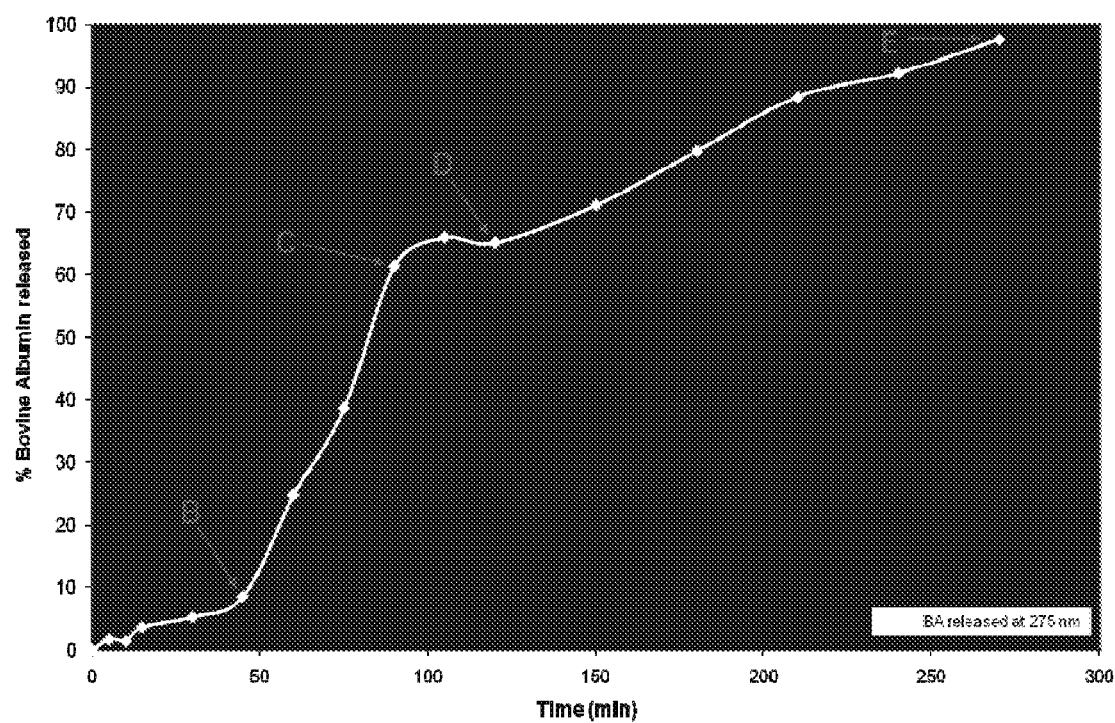
FIG. 10 is a graph that shows the release of bovine serum albumin from glucose recognitive, multilayered systems.

Each of the BSA layers was evenly dispersed upon the polymer disk below it using a spatula. The RTV rubber was then applied as needed. The multilaminate systems that we created were visibly much bulkier than we would prefer; the difficulty of applying such a course material as RTV rubber makes the tablet appear messy and mechanically rigid. Swelling Studies and Release Studies. Studies were done on the swelling and release of these multilaminate systems. These studies show the release of bovine serum albumin from glucose-recognitive planar multilayered systems. FIG. 10 shows the behavior of such systems in a 100 mg/dL solution of glucose. Clearly, all incorporated BSA was released in two pulses. The recognitive layers correspond to regions AB and CD while the releasing layers correspond to regions BC and DE.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue studyation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. E. S. Golub and D. R. Green, Immunology: A Synthesis. 1991, Sunderland, Mass.: Sinauer Assoc.
2. F. Breinl and F. Haurowitz, Chemical Investigation of the Precipitate from Hemoglobin and Anti-hemoglobin Serum and Remarks on the Nature of Antibodies. Z. Physiol. Chem., 1930. 192: p. 45.
3. L. Pauling, A Theory of the Structure and Process of Formation of Antibodies. J. Am. Chem. Soc., 1940. 62: p. 2643-2657.
4. N. K. Jerne, The Natural Selection Theory of Antibody Formation. Proc. Natl. Acad. Sci. USA, 1955. 41: p. 849.
5. D. W. Talmage, Allergy and Immunology. Ann. Rev. Med., 1957. 8: p. 239.
6. F. M. Burnet, A Modification of Jerne's Theory of Antibody Production Using the Concept of Clonal Selection. Aust. J. Sci., 1957. 20: p. 67.
7. D. R. Davies and S. Chacko, Antibody Structure. Accounts Chem. Res., 1993. 26: p. 421-427.
8. N. K. Jerne, The Generative Grammar of the Immune System, in Nobel Lectures, Physiology or Medicine 1981-1990, J. Lindsten, Editor. 1993, World Scientific Publishing Co.: Singapore. p. 211-225.
9. G. Köhler and C. Milstein, Continuous cultures of fused cells secreting antibody of predefined specificity. Nature, 1975. 256: p. 495-497.
10. G. J. F. Köhler, Derivation and Diversification of Monoclonal Antibodies, in Nobel Lectures, Physiology or Medicine 1981-1990, J. Lindsten, Editor. 1993, World Scientific Publishing Co.: Singapore. p. 228-243.
11. C. Milstein, From the Structure of Antibodies to the Diversification of the Immune Response, in Nobel Lectures, Physiology or Medicine 1981-1990, J. Lindsten, Editor. 1993, World Scientific Publishing Co.: Singapore. p. 248-270.
12. R. B. Merrifield, Solid Phase Peptide Synthesis. I. The Synthesis of a Tetrapeptide. J. Am. Chem. Soc., 1963. 85: p. 2149-2154.
13. R. B. Merrifield, Solid Phase Peptide Synthesis. II. The Synthesis of Bradykinin. J. Am. Chem. Soc., 1964. 86: p. 304.
14. R. B. Merrifield, Solid-Phase Peptide Synthesis, III. An Improved Synthesis of Bradykinin. Biochem., 1964. 3: p. 1385-1390.
15. B. Merrifield, Solid Phase Synthesis, in Nobel Lectures, Chemistry 1981-1990, T. Frängsmyr, Editor. 1992, World Scientific Publishing Co.: Singapore. p. 149-175.
16. K. Kirshenbaum, A. E. Barron, R. A. Goldsmith, P. Armand, E. K. Bradley, K. T. V. Truong, K. A. Dill, F. E. Cohen, and R. N. Zuckermann, Sequence-specific polypeptoids: A diverse family of heteropolymers with stable secondary structure. Proc. Natl. Acad. Sci. USA, 1998. 95: p. 4303-4308.
17. M. Egholm, E. Buchardt, P. E. Nielsen, and R. H. Berg, Peptide nucleic acids (PNA). Oligonucleotide analogues with an achiral peptide backbone. J. Am. Chem. Soc., 1992. 114: p. 1895-1897.
18. G. P. Dado and S. H. Gellman, Intramolecular Hydrogen Bonding in Derivatives of Beta-Alanine and Gamma-Amino Butyric Acid: Model Studies for the Folding of Unnatural Polypeptide Backbones. J. Am. Chem. Soc., 1994. 116: p. 1054-1062.
19. D. H. Appella, L. A. Christianson, I. L. Karle, D. R. Powell, and S. H. Gellman, Peptide Foldamers: Robust Helix Formation in a New Family of Beta-Amino Acid Oligomers. J. Am. Chem. Soc., 1996. 118: p. 13071-13072.
20. K. Yue and K. A. Dill, Inverse Protein Folding Problem: Designing Polymer Sequences. Proc. Natl. Acad. Sci. USA, 1992. 89: p. 4163-4167.
21. S. H. Gellman, Foldamers: A Manifesto. Accounts Chem. Res., 1998. 31: p. 173-180.

22. K. Kirshenbaum, R. N. Zuckermann, and K. A. Dill, Designing polymers that mimic biomolecules. Current Opinion in Structural Biology, 1999. 9: p. 530-535.
23. P. Koehl and M. Levitt, De Novo Protein Design. I. In Search of Stability and Specificity. J. Mol. Biol., 1999. 293: p. 1161-1181.
24. P. Koehl and M. Levitt, De Novo Protein Design. II. Plasticity in Sequence Space. J. Mol. Biol., 1999. 293: p. 1183-1193.
25. E. I. Shakhnovich and A. M. Gutin, Engineering of stable and fast-folding sequences of model proteins. Proc. Natl. Acad. Sci. USA, 1993. 90: p. 7195-7199.
26. V. S. Pande, A. Y. Grosberg, and T. Tanaka, Folding Thermodynamics and kinetics of imprinted renaturable heteropolymers. J. Chem. Phys., 1994. 101(9): p. 8246-8257.
27. V. S. Pande, A. Y. Grosberg, and T. Tanaka, Thermodynamic procedure to synthesize heteropolymers that can renature to recognize a given target molecule. Proc. Natl. Acad. Sci. USA, 1994. 91: p. 12976-12979.
28. V. S. Pande, A. Y. Grosberg, and T. Tanaka, Phase diagram of heteropolymers with an imprinted conformation. Macromolecules, 1995. 28: p. 2218-2227.
29. V. S. Pande, A. Y. Grosberg, and T. Tanaka, How to Create Polymers with Protein-Like Capabilities: A Theoretical Suggestion. Physica D, 1997. 107: p. 316-321.
30. K. Mosbach and O. Ramstrom, The Emerging Technique of Molecular Imprinting and its Future Impact on Biotechnology. Biotechnol., 1996. 14: p. 163-170.
31. P. A. G. Cormack and K. Mosbach, Molecular imprinting: recent developments and the road ahead. Reactive and Functional Polymers, 1999. 41: p. 115-124.
32. K. Mosbach, Toward the next generation of molecular imprinting with emphasis on the formation, by direct molding, of compounds with biological activity (biomimetics). Anal. Chim. Acta, 2001. 435: p. 3-8.
33. M. Komiyama, T. Takeuchi, T. Mukawa, and H. Asanuma, Molecular Imprinting From Fundamentals to Applications. 2003, Weinheim, Germany: Wiley-VCH.
34. G. Wulff, A. Sarhan, and K. Zabrocki, Enzyme-Analogue Built Polymers and Their Use for the Resolution of Racemates. Tetrahedron Letters, 1973. 44: p. 4329-4332.
35. C. Yu and K. Mosbach, Influence of mobile phase composition and cross-linking density on the enantiomeric recognition properties of configurationally biomimetic imprinted polymers. J. Chromatogr. A, 2000. 888: p. 63-72.
36. H. S. Andersson, J. G. Karlsson, S. A. Piletsky, A.-C. Koch-Schmidt, K. Mosbach, and I. A. Nicholls, Study of the nature of recognition in configurationally biomimetic imprinted polymers, II. Influence of monomer-template ratio and sample load on retention and selectivity. J. Chromatogr. A, 1999. 848: p. 39-49.
37. D. Kriz, C. B. Kriz, L. I. Anderson, and K. Mosbach, Thin-Layer Chromatography Based on the Molecular Imprinting Technique. Anal. Chem., 1994. 66: p. 2636-2639.
38. J. Cederfur, Y. Pei, M. Zihui, and M. Kempe, Synthesis and Screening of a Configurationally biomimetic imprinted Polymer Library Targeted for Penicillin G. J. Comb. Chem., 2003. 5: p. 67-72.
39. M. Kempe and K. Mosbach, Separation of amino acids, peptides and proteins on configurationally biomimetic imprinted stationary phases. J. Chromatogr. A, 1995. 691: p. 317-323.
40. K. Haupt, K. Noworytab, and W. Kutner, Imprinted polymer-based enantioselective acoustic sensor using a quartz crystal microbalance. Anal. Commun., 1999. 36.
41. C. Liang, H. Peng, A. Zhou, L. Nie, and S. Yao, Molecular imprinting polymer coated BAW bio-mimic sensor for direct determination of epinephrine. Anal. Chim. Acta, 2000. 415: p. 135-141.
42. J. Z. Hilt, M. E. Byrne, and N. A. Peppas. Novel Biomimetic Polymer Networks: Development and Application as Selective Recognition Elements for Biomolecules at the Micro-/Nanoscale. in AIChE Nanoscale Science and Engineering Topical Conference Proceedings. 2003. San Francisco, Calif.
43. D. K. Robinson and K. Mosbach, Molecular imprinting of a transition state analogue leads to a polymer exhibiting esterolytic activity. J. Chem. Soc. Chem. Commun., 1989. 14: p. 969-970.
44. B. Sellergren and K. J. Shea, Enantioselective ester hydrolysis catalyzed by imprinted polymers. Tetrahedron-Asymmetry, 1994. 5: p. 1403-1406.
45. R. N. Karmalkar, M. G. Kulkarni, and R. A. Mashelkar, Configurationally biomimetic imprinted Hydrogels Exhibit Chymotrypsin-like Activity. Macromolecules, 1996. 29: p. 1366-1368.
46. O. Ramström and K. Mosbach, Synthesis and catalysis by configurationally biomimetic imprinted materials. Curr. Opin. Chem. Biol., 1999. 3: p. 759-764.
47. L. Andersson, B. Sellergren, and K. Mosbach, Imprinting of Amino Acid Derivatives in Macroporous Polymers. Tetrahedron Letters, 1984. 25(45): p. 5211-5214.
48. G. Vlatakis, L. J. Andersson, R. Muller, and K. Mosbach, Drug assay using antibody mimics made by molecular imprinting. Nature, 1993. 361: p. 645-647.
49. R. A. Bartsch and M. Maeda, eds. Molecular and Ionic Recognition with Imprinted Polymers. ACS Symposium Series. 1998, ACS: Washington, D.C.
50. L. I. Andersson, Molecular Imprinting as an Aid to Drug Bioanalysis, in Drug Development Assay Approaches, Including Molecular Imprinting and Biomarkers, E. Reid, H. M. Hill, and I. D. Wilson, Editors. 1998, The Royal Society of Chemistry: Cambridge, UK.
51. G. Odian, Principles of Polymerization. 1991, New York: Wiley.
52. G. Wulff, J. Vietmeier, and H.-G. Poll, Enzyme-analogue built polymers, 22: Influence of the nature of the crosslinking agent on the performance of imprinted polymers in racemic resolution. Makromolekul. Chem., 1987. 188: p. 731-740.
53. B. D. Ratner, The Engineering of Biomaterials Exhibiting Recognition and Specificity. J. Mol. Recognition, 1996. 9: p. 617-625.
54. N. A. Peppas and R. Langer, Advances in Biomaterials, Drug Delivery, and Bionanotechnology. AIChE J., 2003. 49(12): p. 2990-3006.
55. M. E. Byrne, K. Park, and N. A. Peppas, Molecular imprinting within hydrogels. Adv. Drug Deliver. Rev., 2002. 54(1): p. 149-161.
56. M. E. Byrne, K. Park, and N. A. Peppas. Biomimetic Networks for Selective Recognition of Biomolecules. 2002: Materials Research Society.
57. J. Z. Hilt, A. K. Gupta, R. Bashir, and N. A. Peppas, Ultrasensitive Biomems Sensors Based on Microcantilevers Patterned with Environmentally Responsive Hydrogels. Biomedical Microdevices, 2003. 5(3): p. 177-184.
58. E. Oral and N. A. Peppas, Responsive and recognitive hydrogels using star polymers. J. Biomed. Mater. Res. A, 2004. 68: p. 439-447.

59. P. Parmpi and P. Kofinas, Biomimetic glucose recognition using configurationally biomimetic imprinted hydrogels. Biomaterials, 2004. 25: p. 1969-1973.

60. L. D. V. Bolisay, J. F. March, W. E. Bentley, and P. Kofinas, Separation of baculoviruses using configurationally biomimetic imprinted polymer hydrogels. Mat. Res. Soc. Symp. Proc., 2004. 787: p. G3.1/1-G3.1/5.

61. D. R. Shnek, D. W. Pack, D. Y. Sasaki, and F. H. Arnold, Specific Protein Attachment to Artificial Membranes via Coordination to Lipid-Bound Copper(I1). Langmuir, 1994. 10: p. 2382-2388.

62. M. Kempe, M. Glad, and K. Mosbach, An approach towards surface imprinting using the enzyme ribonuclease A. J. Mol. Recognition, 1995. 8(1-2): p. 35-39.

63. L. I. Andersson, R. Muller, G. Vlatakis, and K. Mosbach, Mimics of the Binding Sites of Opiod Receptors Obtained by Molecular Imprinting of Enkephalin and Morphine. Proc. Natl. Acad. Sci. USA, 1995. 92: p. 4788-4792.

64. D. L. Venton and E. Gudipati, Influence of protein on polysiloxane polymer formation: evidence for induction of complementary protein-polymer interactions. Biochim. Biophys. Acta, 1995. 1250: p. 126-136.

65. A. Rachkov and N. Minoura, Towards Configurationally biomimetic imprinted Polymers Selective to Peptides and Proteins. The Epitope Approach. Biochimica et Biophysica Acta, 2001. 1544: p. 255-266.

66. L. J. Harris, S. B. Larson, K. W. Hasel, and A. McPherson, Refined Structure of an Intact IgG2a Monoclonal Antibody. Biochem., 1997. 36: p. 1581-1597.

67. H. M. Berman, J. Westbrook, Z. Feng, G. Gilliland, T. N. Bhat, H. Weissig, I. N. Shindyalov, and P. E. Bourne, The Protein Data Bank. Nucleic Acids Res., 2000. 28: p. 235-242.

68. D. R. Burton, Monoclonal Antibodies from Combinatorial Libraries. Accounts Chem. Res., 1993. 26: p. 405-411.

69. J. Tormo, D. Blaas, N. R. Parry, D. Rowlands, D. Stuart, and I. Fita, Crystal Structure of a Human Rhinovirus Neutralizing Antibody Complexed with a Peptide Derived from Viral Capsid Protein VP2. EMBO J., 1994. 13: p. 2247-2256.

70. L. Stryer, Biochemistry. 4th ed. 1995, New York: W. H. Freeman.

71. K. Mosbach, K. Haupt, X.-C. Liu, P. A. G. Cormack, and O. Ramstrom, Molecular Imprinting Status Artis et Quo Vadere, in Molecular and Ionic Recogniton with Imprinted Polymers, R. A. Bartsch and M. Maeda, Editors. 1998, American Chemical Society: Washington, D.C.

OTHER REFERENCES

Burt S. Essential Oils: their antibacterial properties and potential applications in food—a review. International Journal of Food Microbiology 94 (2004) pp. 223-253

Canal, T.; Peppas, N. A. J. Biomed. Mater. Res. (1989) 23, 1183.

Chang C. P., Dobashi T. Preparation of alginate complex capsules containing eucalyptus essential oil and its controlled release. Colloids and Surfaces B: Biointerfaces 32 (2003) pp. 257-262

Duclairoir C., Orecchioni A. M., Depraetere P., Osterstock F., Nakache E. Evaluation of gliadins nanoparticles as drug delivery systems: a study of three different drugs. International Journal of Pharmaceutics, 253 (2003) p. 133-144

Franzios G., Mirotsou M., Hatziapostolou E., Kral J., Scouras Z. G., Mavragani-Tsipidou P. Insecticidal and genotoxic activities of mint essential oils. Journal of Agricultural and Food Chemistry, 45 (1997) pp. 2690-2694

Hartmans K. J., Diepenhorst P. The use of carvone as a sprout inhibitor for potatoes. Potato Research, 37 (1994) pp. 445-446

Hartmans K. J., Lenssen J. M., De Vries R. G. Use of talent (carvone) as a sprout growth regulator of seed potatoes and the effect on stm and tuber number, Potato Research, 41 (1998) pp. 190-191

Muller N. J. United States Patent Application 20020071877 (2002)

Peppas N. A., Am Ende D. J. Controlled release of perfumes from polymers. II. Incorporation and release of essential oils from glassy polymers, Journal of Applied Polymer Science, Vol. 66 (1997) pp. 509-513

Peppas N. A., Brannon-Peppas L. Controlled Release of fragrance from polymers I. Thermodynamic analysis. Journal of Controlled Release 40 (1996) 245-250

Sanchez I. C. Equilibrium distribution of a minor constituent between a polymer and its environment, in Durability of Macromolecular Materials, R. K. Eby, ed. ACS Symp. Ser. Vol. 95, American Chemical Society, Washington, D.C., 1979, pp. 171-181

Sanchez I. C., Chang S. S, and Smith L. E. Migration models for polymer additives, Polym. News 6 (1980) 249-256

Secouard S., Malhiac C., Grisel M., Decroix B. Release of limonene from polysaccharide matrices: viscosity and synergy effect. Food Chemistry 82 (2003) 227-234

What is claimed is:

1. A composition comprising:
    a multi-bilayer polymer tablet comprising
    a first bilayer comprising at least one first molecular imprinted recognition polymeric first layer comprising an imprint that recognizes a template molecule and at least one first active agent in a second layer, wherein the at least one molecular imprinted recognition polymeric first layer recognizes a first template molecule to release the at least one first active agent;
    at least a second bilayer in communication with the first bilayer wherein each second bilayer comprises at least one second molecular imprinted recognition polymeric layer and at least one second active agent in a second layer; and wherein the at least one second molecular imprinted recognition polymeric layer recognizes a second template molecule to release the at least one second active agent, wherein the first bilayer and the at least a second bilayer are compressed into a single tablet,
    wherein the at least one first molecular imprinted recognition polymeric layer and the at least one second molecular imprinted recognition polymeric layer are (poly) methacrylic acid molecular imprinted recognition polymers;
    wherein the at least one first active agent and the at least one second active agent are insulin; and
    wherein the first template molecule and the second template molecule are glucose.

2. The composition of claim 1, wherein
    the at least one second molecular imprinted recognition polymeric layer,
    the at least one molecular imprinted recognition polymeric first layer or both further comprises microparticles.

3. The composition of claim 1, wherein the first bilayer, the at least a second bilayer or both further comprise at least one of an adhesive, a binder, an inactive matrix or an excipient.

4. The composition of claim 1, wherein the at least one second molecular imprinted recognition polymeric layer, the at least one first molecular imprinted recognition polymeric layer or both is at least one of biocompatible, biodegradable, swellable, water-soluble, or porous.

5. The composition of claim 1, wherein the recognitive portion of the bilayer unit is disrupted due to: osmosis upon the presence and binding of the molecule leading to rupture due to swelling; change of the solubility of the polymeric network leading to polymer dissolution; local temperature changes leading to expansion of the polymeric network and combinations thereof.

6. The composition of claim 1, further comprising a third layer in communication with the first bilayer, the at least a second bilayer, or both to form a tri-layer and an active agent is loaded into the third layer.

7. The composition of claim 1, wherein the composition comprises 3, 4, 5, 6, 7, 8, 9, 10, 11, 12, 13, 14, 15, 16, 17, 18, 19 or 20 layers.

8. The composition of claim 1, wherein the at least one first active agent, the at least one second active agent or both are pharmaceuticals.

9. The composition of claim 1, wherein the multi-bilayer polymer tablet further comprises a coating.

10. The composition of claim 1, wherein the multi-bilayer polymer tablet is a sphere, film, planar, semi-spherical, cylinder, rod, hemispheres, conical, hemi-cylinders, bi-layer and combination thereof.

11. A composition comprising:
a bilayer polymer tablet comprising at least 2 bilayers wherein each of the at least 2 bilayers comprise:
a first molecular imprinted recognition layer comprising a molecular imprinted recognition polymer comprising poly methacrylic acid comprising an imprint that recognizes a template molecule and
a second active agent layer in contact with the first molecular imprinted recognition layer comprising an active agent wherein the molecular imprinted recognition polymer recognizes a template molecule and exposes the second active agent layer to release the active agent, wherein the first molecular recognition and second active agent layers are compressed into a single tablet wherein the active agent is insulin; and the template molecule is glucose.

12. The composition of claim 11, wherein the molecular imprinted recognition polymer further comprises microparticles.

13. The composition of claim 11, further comprising at least one of an adhesive, a binder, an inactive matrix or an excipient in the first molecular imprinted recognition layer, the second active agent layer or both.

14. The composition of claim 11, wherein the molecular imprinted recognition polymer is at least one of biocompatible, biodegradable, swellable, water-soluble, or porous.

15. The composition of claim 11, wherein the recognitive portion of the bilayer polymer tablet is disrupted due to: osmosis upon the presence and binding of the molecule leading to rupture due to swelling; change of the solubility of the polymeric network leading to polymer dissolution; local temperature changes leading to expansion of the polymeric network and combinations thereof.

16. The composition of claim 11, wherein the active agent is loaded into two or more layers.

17. The composition of claim 11, wherein active agent is selected from pharmaceuticals.

18. The composition of claim 11, wherein the bilayer polymer tablet further comprises a coating.

19. The composition of claim 11, wherein the bilayer polymer tablet is a sphere, film, planar, semi-spherical, cylinder, rod, hemispheres, conical, hemi-cylinders and combination thereof.

20. The composition of claim 11, wherein the composition comprises 3, 4, 5, 6, 7, 8, 9, 10, 11, 12, 13, 14, 15, 16, 17, 18, 19 or 20 layers.

* * * * *